US010018609B2

(12) United States Patent
Miller et al.

(10) Patent No.: US 10,018,609 B2
(45) Date of Patent: Jul. 10, 2018

(54) INFRARED-BASED ICE FORMATION DETECTION SYSTEMS AND METHODS

(71) Applicant: FLIR Systems, Inc., Wilsonville, OR (US)

(72) Inventors: John Lester Miller, Lake Oswego, OR (US); Joel Hansen, Beaverton, OR (US); Noel Jolivet, Lake Oswego, OR (US); Cynthia Archer, Sherwood, OR (US); Kateri E. Paul, Medford, MA (US)

(73) Assignee: FLIR Systems, Inc., Wilsonville, OR (US)

( * ) Notice: Subject to any disclaimer, the term of this patent is extended or adjusted under 35 U.S.C. 154(b) by 0 days.

(21) Appl. No.: 15/059,263

(22) Filed: Mar. 2, 2016

(65) Prior Publication Data

US 2016/0178593 A1 Jun. 23, 2016

Related U.S. Application Data

(63) Continuation of application No. PCT/US2014/053753, filed on Sep. 2, 2014.
(Continued)

(51) Int. Cl.
*G01N 33/18* (2006.01)
*G06K 9/00* (2006.01)
(Continued)

(52) U.S. Cl.
CPC ......... *G01N 33/18* (2013.01); *G01N 21/3563* (2013.01); *G01N 21/3577* (2013.01);
(Continued)

(58) Field of Classification Search
CPC ... G06T 7/0028; G06T 7/0081; G06K 9/6202; G06K 9/6267
(Continued)

(56) References Cited

U.S. PATENT DOCUMENTS

| 4,808,824 A | 2/1989 | Sinnar |
| 5,963,148 A | 10/1999 | Sekine et al. |
| 2008/0129541 A1 | 6/2008 | Lu et al. |

FOREIGN PATENT DOCUMENTS

JP 2007232652 9/2007

OTHER PUBLICATIONS

S. Jaggi, "A two-channel PC-based hardware implementation of the maximum likelihood classifier for the shuttle ice detection system", Lockheed Engineering & Sciences Company, Apr. 7, 1991, 591-595 pgs, Proceedings of Southeast Conference, IEEE, Williamsburg, New York.
(Continued)

*Primary Examiner* — Ruiping Li
(74) *Attorney, Agent, or Firm* — Haynes and Boone, LLP

(57) ABSTRACT

Techniques are disclosed for systems and methods using infrared imaging modules to image and detect phase transitions of water, such as ice formation, in a scene. An ice formation detection system may include one or more infrared imaging modules, a logic device, and a communication module. The infrared imaging modules may be positioned to image a scene in which ice formation is to be detected. The logic device may be adapted to process captured infrared images to detect ice formation in the scene. The logic device may also be adapted to use the communication module to report detected ice formation to an indicator, a display, a user interface, and/or an ice formation mitigation system.

20 Claims, 8 Drawing Sheets

Related U.S. Application Data

(60) Provisional application No. 61/873,302, filed on Sep. 3, 2013.

(51) Int. Cl.

| | | |
|---|---|---|
| *G06K 9/20* | (2006.01) | |
| *G01N 21/3563* | (2014.01) | |
| *G01N 21/3577* | (2014.01) | |
| *G06K 9/46* | (2006.01) | |
| *G06K 9/62* | (2006.01) | |
| *H04N 5/225* | (2006.01) | |
| *H04N 5/33* | (2006.01) | |
| *G06T 7/33* | (2017.01) | |
| *G06T 7/11* | (2017.01) | |

(52) U.S. Cl.
CPC ..... *G06K 9/00624* (2013.01); *G06K 9/00791* (2013.01); *G06K 9/2018* (2013.01); *G06K 9/4661* (2013.01); *G06K 9/6202* (2013.01); *G06K 9/6267* (2013.01); *G06T 7/11* (2017.01); *G06T 7/33* (2017.01); *H04N 5/2256* (2013.01); *H04N 5/332* (2013.01); *G01N 2033/1873* (2013.01); *G06T 2207/10016* (2013.01); *G06T 2207/10048* (2013.01)

(58) Field of Classification Search
USPC .......................................................... 382/191
See application file for complete search history.

(56) References Cited

OTHER PUBLICATIONS

Jonsson, Patrik, "Remote Sensor for Winter Road Surface Status Detection", Dept. of Information Technology and Media, Oct. 28, 2011, 1285-1288 pgs, 2011 IEEE Sensors Proceedings, Limerick, Ireland.

M. Kutila et al., "Optical Road-State Monitoring for Infrastructure-side co-operative traffic safety systems", 2008 IEEE Intelligent Vehicles Symposium, Jun. 4-6, 2008, 620-625 pgs, Eindhoven University of Technology, Piscataway, New Jersey.

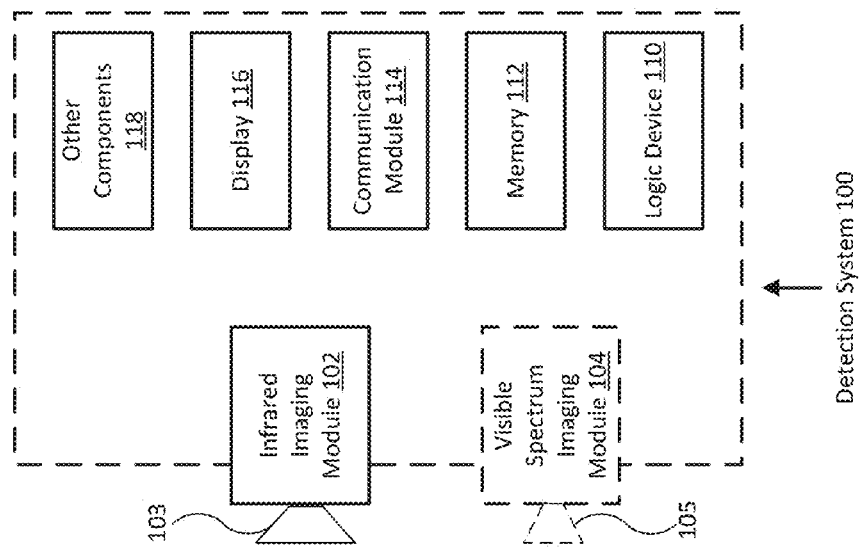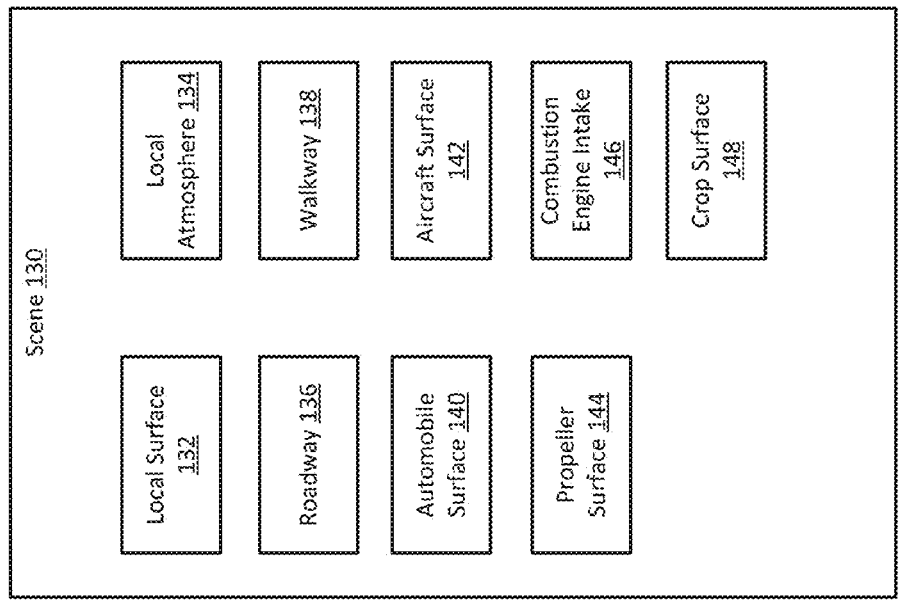
FIG. 1

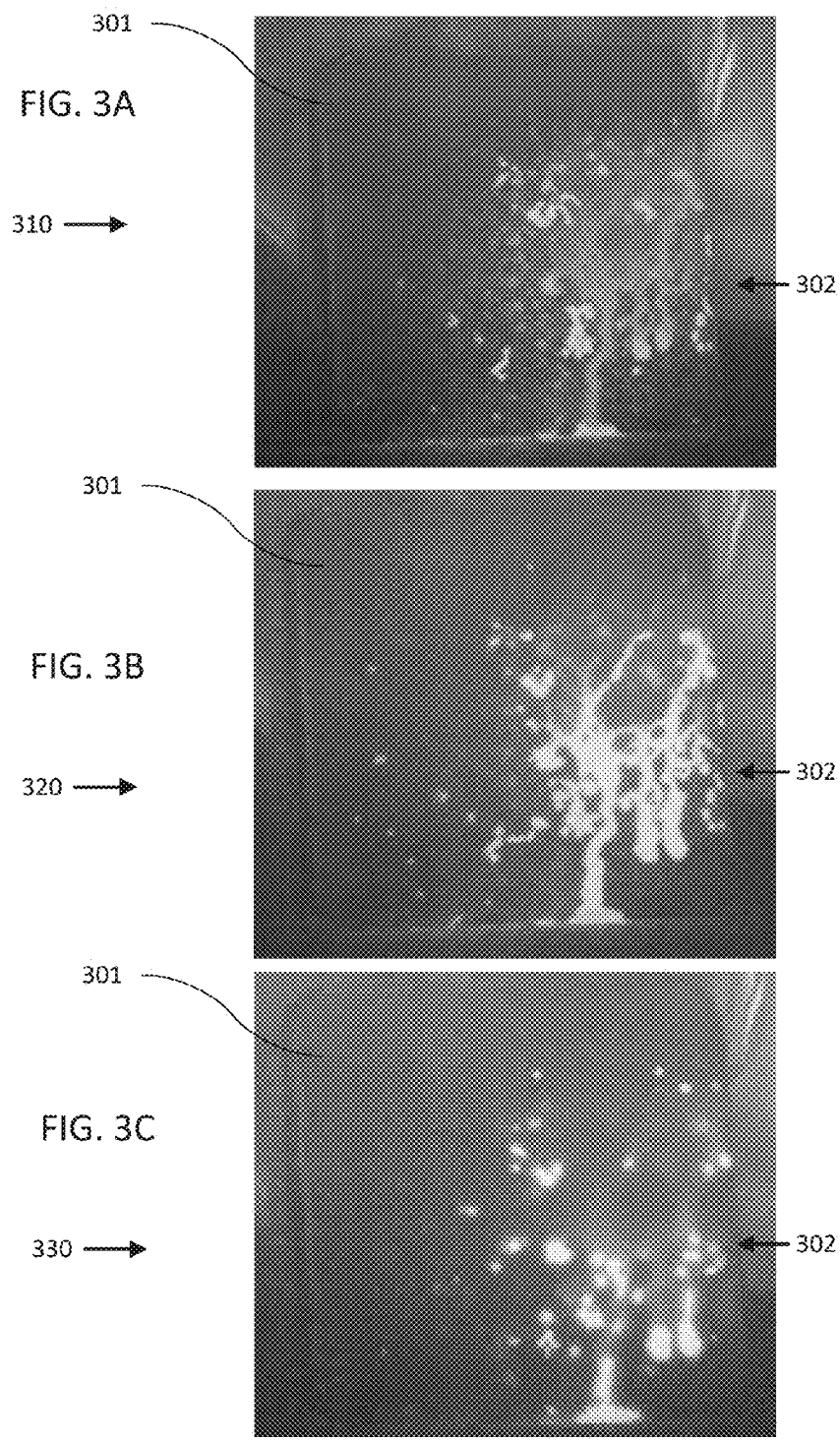

802  ↑
     810

802  ↑
     820

802  ↑
     830

802  ↑
     840

INFRARED-BASED ICE FORMATION DETECTION SYSTEMS AND METHODS

CROSS-REFERENCE TO RELATED APPLICATIONS

This application is a continuation of International Application No. PCT/US2014/053753 filed Sep. 2, 2014 and entitled "INFRARED-BASED ICE FORMATION DETECTION SYSTEMS AND METHODS," which is hereby incorporated by reference in its entirety.

International Application No. PCT/US2014/053753 filed Sep. 2, 2014 claims priority to and the benefit of U.S. Provisional Patent Application No. 61/873,302 filed Sep. 3, 2013 and entitled "INFRARED-BASED ICE FORMATION DETECTION SYSTEMS AND METHODS," which is hereby incorporated by reference in its entirety.

TECHNICAL FIELD

One or more embodiments of the invention relate generally to imaging systems and more particularly, for example, to systems and methods for detecting ice formation using infrared imaging.

BACKGROUND

Ice formation presents an ongoing safety hazard in the operation of a multitude of mechanical systems, including power generation systems and a variety of transportation systems. For example, ice formation on aircraft surfaces presents a particular problem because it can quickly reduce the available power to lift ratio and result in unplanned and often catastrophic groundings. Undetected ice formation on other surfaces, such as walkways and roadways, can cause costly slip-related accidents for pedestrians and road vehicles, and any ice formation on crops can decimate yield in hours.

Conventional systems used to mitigate the problems associated with ice formation are typically inefficient and/or costly, and they often aren't timely or reliable enough in their ability to detect ice formation to allow for preemptive measures targeted to the specific areas and/or time periods experiencing ice formation. Instead, conventional mitigation systems waste energy and other resources either on applying measures when and/or where they aren't needed, or on melting or otherwise removing substantial aggregations of ice after they've formed and caused damage and/or general interruption of normal operation. Thus, there is a need for an improved methodology for detecting ice formation that is cost effective and substantially real-time and that can be used to detect ice formation in a variety of contexts reliably.

SUMMARY

Techniques are disclosed for systems and methods using infrared imaging modules to image and detect phase transitions of water, such as ice formation, in a scene. In one embodiment, a phase transition detection system may include one or more infrared imaging modules, a logic device, and a communication module. The infrared imaging modules may be positioned to image a scene in which a phase transition of water is to be detected. The logic device may be adapted to process captured infrared images to detect phase transitions of water in the scene. The logic device may also be adapted to use the communication module to report detected phase transitions to an indicator, a display, a user interface, and/or an ice formation mitigation system.

In one embodiment, a detection system includes an infrared imaging module, a communication module, and a logic device in communication with the infrared imaging module and communication module. In such embodiment, the logic device may be adapted to capture infrared images of a scene using the infrared imaging module; process the infrared images; and detect one or more phase transitions of water in the processed infrared images of the scene. In some embodiments, the logic device may be adapted to report the detection of the one or more phase transitions using the communication module.

In another embodiment, a method includes capturing infrared images of a scene using an infrared imaging module; processing the infrared images; and detecting one or more phase transitions of water in the processed infrared images of the scene. In some embodiments, the method may include reporting the detection of the one or more phase transitions using a communication module.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 1 illustrates a block diagram of an ice formation detection system in accordance with an embodiment of the disclosure.

FIGS. 3A-3C depict a series of infrared images illustrating transient characteristics of the formation of ice on a rubber surface in accordance with an embodiment of the disclosure.

Embodiments of the invention and their advantages are best understood by referring to the detailed description that follows. It should be appreciated that like reference numerals are used to identify like elements illustrated in one or more of the figures.

DETAILED DESCRIPTION

Figure 2:
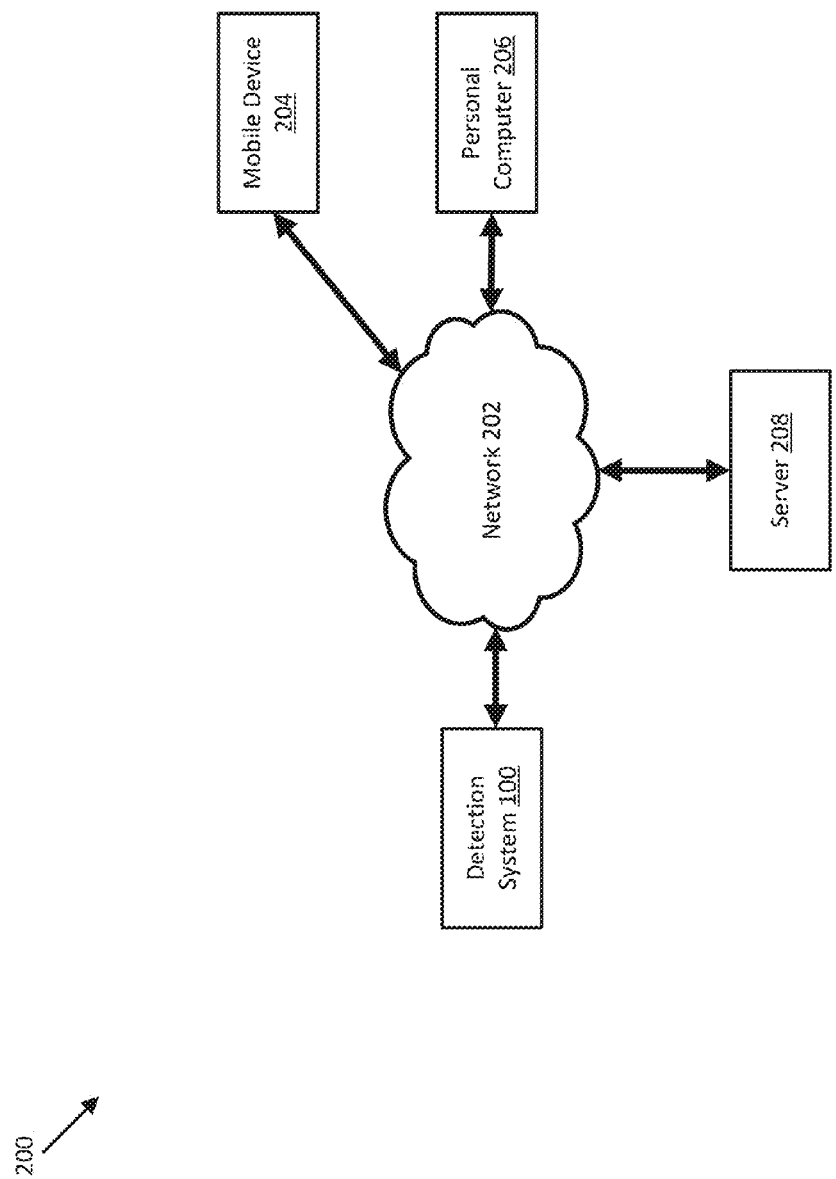
FIG. 2 illustrates a block diagram of a networked ice formation detection system in accordance with an embodiment of the disclosure.

In accordance with various embodiments of the present disclosure, ice formation detection systems and methods may advantageously include one or more infrared imaging modules, a logic device, and a communication module. The system may be adapted to capture infrared images of a scene (e.g., a view of an aircraft wing), process the infrared images to detect a phase transition of water in the scene (e.g., liquid to ice and/or ice to liquid), and to report detection of a phase transition. In various embodiments, the system can be adapted to detect and report phase transitions of water in a scene substantially in real time.

For example, it is known that the phase transition of liquid water to ice is exothermic and can cause a rise in temperature in its surroundings and, likewise, that the phase transition of ice to liquid is endothermic and can cause a drop in temperature in its surroundings, where the surroundings may include materials or a surface in contact with the water, for example, or may include portions of the water not yet undergoing a phase transition. The commensurate rise or drop in temperature can be detected and/or measured using an infrared imaging module and various image processing techniques, as described herein, and the detection can be reported to an indicator, a display, a user interface, an ice formation mitigation system, and/or other portions of a detection system, for example, to mitigate and/or take advantage of the effects and/or timing of the phase transition.

In addition, phase transitions in water may be evidenced by crystal formation having one or more characteristic orientations dependent on, for example, surface tension interaction with a particular surface, temperature and/or a time evolution of temperature (e.g., temperature profile) at a particular interface (e.g., water-surface and/or water-atmosphere), and/or other environmental conditions. Moreover, the characteristic orientations may tilt or change over time during a phase transition, and those changes can also be dependent on various environmental conditions. Both crystal formation and changes in crystal orientation may reflect infrared radiation (e.g., ambient and/or active illumination) in patterns and/or with other transient characteristics, as described herein, and those transients can be detected and/or measured using an infrared imaging module (e.g., as changes in intensity and/or wavelength, for example) and various image processing techniques, also described herein. Furthermore, crystal destruction/disorganization and/or associated structural changes due to melting can also be detected using similar methods. As noted above, detections can be reported to an indicator, a display, a user interface, an ice formation mitigation system, and/or other portions of a detection system, for example, to mitigate and/or take advantage of the effects and/or timing of the phase transition.

The various changes (e.g., in temperature, in crystal structure) associated with phase transitions in water can take place over fractions of a second, seconds, or minutes, and specific characteristics of the changes (e.g., amplitude, emission wavelength, time evolution, spatial pattern, and/or other transient characteristics) may depend on a variety of environmental conditions and/or gradients in those conditions, such as atmospheric pressure, temperature, humidity, surface texture and/or chemistry (e.g., attributes affecting thermal exchange between water and a surface), thermal properties of a surface (e.g., relative temperature, thermal conductivity, heat capacity), size and shape of the bulk water (e.g., droplets, ice crystals), kinetic motion of the water or an impact surface, and/or other environmental conditions, for example.

In some embodiments, where the detected phase transition indicates the formation of ice, the corresponding measured temperature increases may range from fractions of a degree Celsius to more than twenty degrees Celsius, for example, depending on various initial and evolving environmental conditions. Onset of a temperature increase associated with the formation of ice may take a fraction of a second, for example, and the measured temperature increase may thereafter saturate at a peak temperature and then decay back to approximately the starting temperature over a time period ranging from fractions of a second to more than twenty seconds, depending on the thermal exchange between the water and its surroundings.

In embodiments where the water is in the form of a droplet moving through the atmosphere, the temperature increase and/or the change in crystal structure corresponding to the formation of ice may present as a point and/or streak (e.g., depending on the velocity of the droplet and the exposure time of the infrared imaging module) of higher intensity infrared radiation localized to the position of the droplet as it is imaged. In embodiments where the water is in contact with a surface, the formation of ice (and the corresponding localized temperature increases and higher intensity infrared radiation) can germinate on and then evolve across the surface in patterns having distinctive spatial and time-based characteristics dependent, at least in part, on the type of material and other properties of the surface. Examples of such patterns are described more fully herein with reference to FIGS. 2A through 3C.

In accordance with embodiments of the present disclosure, detection of the formation of ice in any context may involve distinguishing the corresponding increases in infrared radiation from other portions or aspects of an imaged scene, for example, and may include a variety of image and signal processing techniques, such as bandpass filtering (e.g., single or multi-band), level filtering, contrast and/or gain control, pattern recognition, and/or a combination of image processing adapted to the environmental conditions and/or the expected behavior of water in a particular set of environmental conditions, as described herein. For example, a particular filter may include a dynamic range adjustment (e.g., gain and/or offset) filter adapted to emphasize a particular range of intensities associated with an expected phase transition transient characteristic. Likewise, a particular filter may include a bandpass filter with one or more relatively narrow passbands corresponding to a particular range of wavelengths associated with an expected phase transition transient characteristic. In some embodiments, such bandpass filter may be used in conjunction with an active illumination device, such as a laser module.

In other embodiments, where the detected phase transition indicates the melting of ice, the corresponding measured temperature and/or infrared radiation decreases can be detected using similar methods to those described herein with respect to the formation of ice, except that detection of the melting of ice involves distinguishing corresponding decreases in infrared radiation from other portions or aspects of an imaged scene. Each signal processing technique or module may be embodied in a physical device, such as a physical filter or filters placed between the infrared imaging module and an imaged scene, or may be embodied in software and/or a combination of physical device and software.

The time needed to reliably detect and report a phase transition of water in a scene is thus dependent on the initial onset of a temperature change caused by the transition, the transmission time of the infrared radiation to the infrared imaging module, the time associated with capturing and processing one or more images captured using the infrared imaging module, and/or the time associated with communicating the results of the processing to an indicator, a mitigation system, and/or other portions of a detection system. Reliable detection times may range from a fraction of a second to five or ten seconds from the onset of a phase transition of water in an imaged scene, depending on various environmental conditions associated with the scene.

Because embodiments of the present disclosure may detect the formation of ice in specific areas and substantially in real time (e.g., prior to build-up of a large volume of ice), a variety of relatively efficient mitigation techniques may be employed. For example, by detecting the early and initial formation of ice on a surface, a corresponding surface heater may be turned on only when ice begins to form and only in areas where the ice is forming. This substantially reduces the total energy needed to counteract the formation of ice on the surface because thicker and/or more extensive layers of ice can require more energy and be more difficult to melt, and because little energy is wasted heating areas where no ice is forming. Further, the heater may be energized to the minimal extent necessary to counteract the environmental conditions causing the formation of ice, for example, by detecting the subsequent melting of ice on the surface (e.g., also substantially in real time). Moreover, more drastic mitigation techniques (e.g., suspension of normal operation, diversion of an aircraft) may be used only in timely response to detecting significant formation of ice on a surface without detection of subsequent melting. In a similar example, operation of a pre-heater used to protect an inlet of a combustion engine (e.g., a gas turbine) from ingesting significant amounts of atmospheric ice may be similarly modulated to counteract the environmental conditions causing formation of atmospheric ice at the inlet.

Other embodiments of the present disclosure may be adapted to provide various productivity and safety features in a wide range of contexts, such as reliable and timely warning of slippery conditions for roadways and walkways, or localized and timely detection of ice formation on crops.

FIG. 1 illustrates a block diagram of a detection system 100 adapted to detect phase transitions of water in scene 130 in accordance with an embodiment of the disclosure. Scene 130 may be any one or combination of views of static, moving, surface, or atmospheric regions on or in which a phase transition of water may occur, as described herein. Views 132-150 provide a non-exclusive list of example contents of scene 130 and are described more fully below. Once a phase transition of water is detected by system 100, system 100 may be adapted to report the detection and help mitigate (e.g., enable an ice removal system upon detection of ice formation, or provide a safety warning or alert) or take advantage of (e.g., disable an ice removal system upon detection of ice melting, or discontinue a safety warning or alert) the circumstances of the detected phase transition.

For example, a local surface 132 may include a view of one or more surfaces, such as a roadway 136, a walkway 138, an automobile surface 140, an aircraft surface 142, a propeller surface 144, a crop surface 148 (e.g., the surfaces of oranges on one or more orange trees), and/or other surfaces imaged by a stationary or mobile embodiment of system 100. System 100 may be adapted to capture infrared images of local surface 132, process the infrared images to detect one or more phase transitions of water on one or more surfaces of local surface 132, and then report the detection of the one or more phase transitions to a mitigation and/or notification system associated with local surface 132. In some embodiments, system 100 may report the detection of the phase transitions by generating an image overlay indicating a position or region of the detected phase transitions in infrared images captured by system 100, and then transmitting the image overlay and at least one corresponding image to a display. In other embodiments, system 100 may report detections by energizing an LED indicator and/or transmitting an alert or notification signal to a component (e.g., an alarm, or an electrical switch or relay) of a mitigation and/or notification system.

In one embodiment, system 100 may be adapted to detect phase transitions of water on roadway 136 (e.g., a street, highway, and/or aircraft runway). For example, system 100 may be mounted to a stationary structure so as to capture substantially static infrared images of a particular intersection, curve, tunnel entrance, or other portion of roadway 136 where ice formation is particularly dangerous (e.g., where there is foreseeable traffic congestion, changes in speed or direction, or increased likelihood of ice formation). Alternatively, system 100 may be mounted to an automobile so as to capture substantially dynamic infrared images of portions of roadway 136 (e.g., changing from image to image) in the vicinity of the automobile as it travels. In further embodiments, system 100 may be mounted to an overflying aircraft and capture a mixture of substantially static and dynamic infrared images of roadway 136.

As noted herein, individual phase transitions of water may be detected as localized changes in imaged infrared radiation (e.g., changes in temperature and/or crystal structure) with amplitudes, wavelengths, time evolutions, spatial patterns, and/or other transient characteristics that distinguish the phase transitions from image noise and other image content captured by system 100. Moreover, the various transient characteristics are at least partially dependent on various environmental conditions, including the composition and texture of a surface being imaged.

In one embodiment, system 100 may be adapted to detect phase transitions of water in one or more images of roadway 136 by creating a list of pixels or substantially adjoining groups of pixels (e.g., targets) indicating a spatial or temporal temperature difference (e.g., a change in infrared radiation from target to non-target in a single image and/or from image to image in a time series of images) and then eliminating false-positive targets exhibiting amplitudes, wavelengths, time evolutions, spatial patterns, and/or other transient characteristics that do not correspond to the transient characteristics expected in light of sensed or expected environmental conditions.

For example, with respect to static infrared images of roadway 136, system 100 may be adapted to eliminate pixels based, at least in part, on spatial patterns that do not correspond to the spatial patterns expected in light of the composition and texture of roadway 136 (e.g., non-conforming spatial patterns), because imaged spatial patterns are not disrupted or otherwise distorted by relative motion. Similarly, also with respect to static infrared images of roadway 136, system 100 may be adapted to eliminate pixels or targets based, at least in part, on non-conforming temporal evolutions (e.g., temperature changes with onset time periods and relaxation time periods that do not correspond to sensed or expected environmental conditions). By contrast, system 100 typically cannot rely on temporal evolutions or spatial patterns to eliminate targets in dynamic infrared images of roadway 136 because both transient characteristics are disrupted or distorted by relative motion.

Once system 100 has eliminated false-positive targets from the target list using reliable, context specific transient characteristics, system 100 may be adapted to report one or more non-eliminated targets (e.g., detection of one or more phase transitions of water on roadway 136). For example, system 100 may be configured to report detections by generating an image overlay indicating presence, type, and position of the phase transitions on a static or dynamic infrared image of roadway 136, and then distribute the report to automobile or aircraft users, safety devices within nearby automobiles or aircraft, and/or other notification and/or mitigation systems over a network, such as a lighted roadside warning sign, for example, or a surface heater for roadway 136. In one embodiment, where system 100 is mounted to an automobile or aircraft, system 100 may be configured to report detections by generating a signal to energize/de-energize an indicator and/or enable/disable a cruise control mode controller of the automobile or aircraft, for example, or otherwise notify a user of the automobile or aircraft of the detections. In some embodiments, system 100 may report detections by providing raw infrared images of scene 130 to display 116 for a user to view.

In the context of roadway 136, system 100 provides increased safety over conventional slip-prevention and ice detection or prevention systems by detecting the formation of ice substantially in real time and potentially before enough ice has formed to cause loss of automobile or aircraft control. Furthermore, system 100 provides increased energy efficiency and reduced congestion by enabling and disabling notification and mitigation techniques according to the substantially real time conditions of roadway 136. With respect to use in overflying aircraft, relatively large and/or disparate portions of roadway 136 may be monitored substantially simultaneously without a need for an expensive stationary installation.

In some embodiments, system 100 may include a variety of local and/or remote environmental sensors that can be used to detect environmental conditions of an imaged scene (e.g., roadway 136). System 100 may be adapted to vary expected transient characteristics of phase transitions of water in response to user input and/or variations in environmental conditions associated with a particular scene, for example, and dependence of transient characteristics on environmental conditions for a particular scene may be based on parameters provided by a user (e.g., indicating a particular surface type or characteristic, indicating an expected range of time evolution) and/or on one or more of historical profiling using various environmental sensors and iterative algorithmic training.

In a related embodiment, system 100 may be implemented with sets of surface characteristics for a number of different surfaces, for example, and may be adapted to recognize an imaged surface and select its corresponding set of surface characteristics based on its appearance and/or its measured response to various environmental conditions, for example. In a further related embodiment, system 100 may be implemented with a set of surface characteristics for a specific surface that forms a known portion of scene 130 (e.g., of any of the views listed with respect to scene 130). In such embodiment, system 100 may be adapted to use the prior knowledge of both the set of surface characteristics and the known portion of scene 130 to more reliably detect phase transitions of water in scene 130. For example, the specific surface forming the known portion of scene 130 may be adapted to produce easily detected transient characteristics under expected environmental conditions, for example, thereby ensuring very timely and reliable detection of phase transitions of water in at least a portion of scene 130. In some embodiments, the known portion of scene 130 may correspond to a test patch, a safety patch, a marker surface, and/or other type of surface adapted to facilitate use of infrared imaging module 102 to detect phase transitions of water in scene 130 (e.g., to facilitate operation of detection system 100).

In a similar embodiment, system 100 may be adapted to detect phase transitions of water on walkway 138. System 100 may be mounted so as to capture substantially static infrared images of a particular portion of walkway 138 where ice formation is particularly dangerous to pedestrians. Alternatively, system 100 may be mounted to a pedestrian so as to capture substantially dynamic infrared images of portions of walkway 138, or system 100 may be mounted to an overflying aircraft so as to capture a mixture of substantially static and dynamic infrared images of walkway 138. System 100 may be adapted to detect and report detections of phase transitions of water on walkway 138 using methods similar to those described in reference to roadway 136. In addition, in embodiments where system 100 is mounted to a pedestrian, system 100 may be implemented with a strobe light and/or an audible alarm, for example, and can be adapted to flash the strobe and/or sound the alarm to report detection of ice forming nearby.

In another embodiment, system 100 may be adapted to detect phase transitions of water on automobile surface 140. System 100 may be mounted so as to capture substantially static infrared images of a particular portion of automobile surface 140 (e.g., a windshield, or a review mirror), or to capture dynamic infrared images of other portions of automobile surface 140 (e.g., tire tread). System 100 may be adapted to detect and report detections of phase transitions of water on automobile surface 140 using methods similar to those described in reference to static and dynamic infrared images of roadway 136. In addition, system 100 may be adapted to report detection of phase transitions on tire treads, windshields, and review mirrors, for example, by providing signals to selectively modulate vehicle speed controls and defrost heaters according to the timing and type of phase transitions detected.

In further embodiments, system 100 may be adapted to detect phase transitions of water on aircraft surface 142 and/or propeller surface 144. For example, system 100 may be mounted so as to capture substantially static and/or dynamic infrared images of particular portions of aircraft surface 142 where ice formation is particularly dangerous (e.g., a leading or trailing edge of a wing, or other portions of an aircraft surface that provide steering impulse and/or lift). Alternatively, or in addition, system 100 may be mounted so as to capture dynamic infrared images of propeller surface 144 (e.g., an airplane propeller, a helicopter rotor) or other moving portions of an aircraft that provide motive force and/or lift. System 100 may be adapted to detect and report detections of phase transitions of water on aircraft surface 142 and propeller surface 144 using methods similar to those described in reference to static and dynamic images of roadway 136 and/or automobile surface 140. For example, localized temperature changes indicative of phase transitions of water on propeller surface 144 may present as high or low intensity circular streaks or blurred lines.

In addition, system 100 may be implemented with one or more environmental sensors (e.g., pressure and/or temperature sensors) adapted to measure environmental conditions (e.g., atmospheric pressure and surface temperature) at various points along aircraft surface 142 and/or near propeller surface 144. System 100 may be adapted to vary expected transient characteristics based on the detected environmental conditions, similar to the methods discussed in reference to roadway 136. Moreover, system 100 may be configured to report detections by providing signals to selectively modulate cockpit indicators and surface heaters according to the timing and type of phase transitions detected. In one embodiment, system 100 may be configured to report detections by providing one or more signals and/or images indicating one or more corresponding detected environmental conditions.

In a further embodiment, system 100 may be adapted to detect phase transitions of water on crop surface 148 (e.g., the surfaces of fruit or other crops on one or more corresponding trees). For example, system 100 may be mounted so as to capture substantially static images of particular portions of crop surface 148. System 100 may be adapted to detect and report detections of phase transitions of water on crop surface 148 using methods similar to those described in reference to static images of roadway 136. In addition, system 100 may be configured to report detections by providing signals to selectively modulate one or more crop heaters according to the timing and type of phase transitions detected. In some embodiments, system 100 may be mounted to image relatively large contiguous portions of crop surface 148 substantially simultaneously, thereby reducing the number of detection systems necessary to monitor crop surface 148.

In some embodiments, scene 130 may include local atmosphere 134. Local atmosphere may include a view of one or more regions of atmosphere containing water, such as combustion intake 146. System 100 may be adapted to capture infrared images of local atmosphere 134, process the infrared images to detect one or more phase transitions of water in one or more regions of local atmosphere 134, and then report the detection of the one or more phase transitions to a mitigation and/or notification system associated with local atmosphere 134. In some embodiments, system 100 may report the detection of the phase transitions by generating an image overlay indicating a position or region of the detected phase transitions in infrared images captured by system 100, and then transmitting the image overlay and at least one corresponding image to a display. In other embodiments, system 100 may report detections by energizing an LED indicator and/or transmitting an alert or notification signal to a component (e.g., an alarm, or an electrical switch or relay) of a mitigation and/or notification system.

In one embodiment, system 100 may be adapted to detect phase transitions of water in combustion engine intake 146 (e.g., a carburetor intake, a gas turbine intake). For example, system 100 may be mounted so as to capture dynamic infrared images (e.g., because the water is not stationary relative to system 100) of particular regions of combustion engine intake 146 where ice formation is particularly dangerous (e.g., where substantial ice formation can damage the corresponding combustion engine). System 100 may be adapted to detect and report detections of phase transitions of water in combustion engine intake 146 using methods similar to those described in reference to dynamic images of roadway 136 and/or automobile surface 140. For example, localized temperature changes indicative of phase transitions of water in combustion engine intake 146 may present as high or low intensity streaks in directions following the intake path of air into combustion engine intake 146.

In addition, system 100 may be implemented with one or more environmental sensors (e.g., pressure and/or temperature sensors) adapted to measure environmental conditions (e.g., atmospheric pressure and surface temperature) at various points near combustion engine intake 146. For example, a significantly decreased pressure caused by the draw of combustion engine intake 146 can encourage the formation of ice at relatively high temperatures. System 100 may be adapted to vary expected transient characteristics based on the detected environmental conditions, similar to the methods discussed in reference to roadway 136, aircraft surface 142, and propeller surface 144. Moreover, system 100 may be configured to report detections by providing signals to selectively modulate combustion engine performance, operation of pre-heaters, and/or engine indicators according to the timing and type of phase transitions detected. In one embodiment, system 100 may be configured to report detections by providing one or more signals and/or images indicating one or more corresponding detected environmental conditions.

In the embodiment shown in FIG. 1, system 100 includes an infrared imaging module 102, a logic device 110, a memory 112, a communication module 114, a display 116, other components 118, and may optionally include visible spectrum imaging module 104. In some embodiments, system 100 may be implemented with a housing adapted to protect system 100 from environmental conditions associated with space flight, atmospheric flight, and/or outdoor environmental conditions, such as stationary or articulated mounting on a telephone pole or other terrestrial structure, for example, or on an aircraft. In various embodiments, the functionality of one or more components of system 100, as described herein, may be integrated into a single module or device, for example, or may be distributed across multiple systems in wired and/or wireless communication with each other. For example, in one embodiment, system 100 may be implemented as an infrared imaging device that can be configured for stand-alone operation while being worn by a pedestrian traveling on a walkway. In other embodiments, system 100 may be implemented with multiple infrared imaging modules, for example, to detect phase transitions of water across a set of comprehensive views of a particular region or surface.

As shown in FIG. 1, system 100 may include infrared imaging module 102. Infrared imaging module 102 may be implemented as an infrared camera or imaging device utilizing actively cooled or uncooled infrared sensors, for example. Infrared imaging module may be adapted to image near-infrared radiation (NIR), short wavelength infrared radiation (SWIR), mid-wavelength infrared radiation (MWIR), long-wavelength infrared radiation (LWIR), far-infrared radiation (FIR), and/or multi-spectral infrared radiation. In some embodiments, infrared imaging module 102 may be a small form factor infrared camera or imaging device, for example, which may be implemented as an array (e.g., a focal plane array or FPA) of microbolometers in accordance with various embodiments disclosed in U.S. Provisional Patent Application No. 61/793,952 entitled "INFRARED IMAGING ENHANCEMENT WITH FUSION" and filed Mar. 15, 2013, which is hereby incorporated by reference in its entirety, or infrared imaging module 102 may be implemented otherwise where appropriate. Infrared imaging module 102 may include one or more logic devices to process and/or store infrared images, as described herein, and be configured to capture, process, and/or manage infrared images, including thermal images, of at least portions of scene 130. Infrared imaging module 102 may be configured to store and/or transmit captured infrared images according to a variety of different color spaces/formats, such as YCbCr, RGB, and YUV, for example, where radiometric data may be encoded into one or more components of a specified color space/format.

Infrared images captured, processed, and otherwise managed by infrared imaging module 102 may be radiometrically normalized infrared images (e.g., thermal images).

Pixels that make up a captured image may contain calibrated thermal data (e.g., representative of absolute temperatures). Accordingly, in some embodiments, infrared imaging module 102 and/or associated components may be calibrated using appropriate techniques so that infrared images captured by infrared imaging module 102 are calibrated infrared images.

In some embodiments, appropriate calibration processes may be performed periodically by infrared imaging module 102 and/or logic device 110 so that infrared imaging module 102 and its captured infrared images maintain an accurate calibration. In other embodiments, infrared imaging module 102 and/or logic device 110 may be configured to emphasize a desired range or interval of radiometric data, for example, and allocate a dynamic range of one or more components of a resulting infrared image according to the desired range of radiometric data. For example, the desired range may be selected to improve reliability in the detection of phase transitions of water under particular sensed or expected environmental conditions. Thus, a radiometric component of an infrared image may include calibrated radiometric data, un-calibrated radiometric data, and/or adjusted radiometric data.

In various embodiments, infrared imaging module 102 may include optical elements 103 (e.g., infrared transmissive lenses, prisms, reflective mirrors, fiber optics) that guide infrared radiation from scene 130 to sensors (e.g., FPAs) of infrared imaging module 102. Such optical elements may be used when mounting infrared imaging module 102 at a particular field-of-view (FOV)-defined location is otherwise difficult or impossible. For example, a flexible fiber-optic cable may be used to route infrared radiation to infrared imaging module 102 so as to allow for imaging a region within a gas turbine intake manifold. Such optical elements may also be used to suitably define or alter an FOV of infrared imaging module 102. A switchable FOV (e.g., selectable by infrared imaging module 102 and/or logic device 110) may optionally be provided to provide alternating far-away and close-up views of a portion of scene 130, for example, or to provide other alternating perspectives of scene 130.

In some embodiments, one or more of infrared imaging module 102 and/or optical elements 103 may include actuators to provide pan, tilt, and/or zoom operations to adjust a direction and/or width of a FOV of infrared imaging module 102. For example, in some embodiments, infrared imaging module 102 may be implemented as a pan-tilt-zoom (PTZ) camera that may be controlled, for example, by logic device 110.

Logic device 110 may be implemented as any appropriate processing device (e.g., microcontroller, processor, application specific integrated circuit (ASIC), field programmable gate array (FPGA), or other logic device) that may be used by system 100 to execute appropriate instructions, such as software instructions and/or signal processing operations for detecting phase transitions of water in an imaged scene (e.g., provided in memory 112). In some embodiments, at least some portion or some functionality of logic device 110 described herein may be implemented as part of an imaging module (e.g., imaging modules 102, 104), for example, or may be part of or implemented with other existing logic devices of separate systems, such as a server, a personal electronic device (e.g., a mobile phone, smartphone, tablet device, laptop computer, desktop computer), and/or any other device that may be used to process, report, or act on phase transitions detected by system 100. In other embodiments, logic device 110 may be adapted to interface and communicate with various external logic devices and associated components and/or perform various operations in a distributed manner.

In general, logic device 110 may be adapted to interface and communicate with other components of system 100 to perform the methods and processes described herein. For example, logic device 110 may be adapted to capture one or more infrared images of scene 130 using infrared imaging module 102, to process the one or more infrared images to detect a phase transition of water in scene 130, and then to report detection of the phase transition using communication module 114. In one embodiment, logic device 110 may be adapted to use communication module 114 to report detection of the phase transition to display 116 and display an alert notification, for example, or display an infrared image with the location of the phase transition indicated on the infrared image by, for example, an overlay image. In another embodiment, logic device 110 may be adapted to use communication module 114 to establish a wireless communication link with an ice mitigation system, such as surface heater for example, and report detection of ice formation on a corresponding surface to enable the surface heater to melt the detected ice.

In addition, logic device 110 may be adapted to perform a variety of image processing operations to implement a particular phase transition detection method, for example, or to implement a particular reporting method, as described herein. Specific image processing and/or reporting operations may be selected through user interaction and/or in accordance with a particular set of sensed or expected environmental conditions. In some embodiments, logic device 110 may be adapted to determine various environmental conditions of scene 130 from infrared image data captured by infrared imaging module 102 and/or from various other types of environmental sensors.

In various embodiments, logic device 110 may be adapted to perform various infrared image based recognition routines (e.g., spatial pattern, time evolution, and/or other transient characteristics recognition routines) to determine, at least in part, whether to keep or eliminate a target from a target list. In some embodiments, logic device 110 may be adapted to train the various recognition routines to recognize a particular transient characteristic or combination of transient characteristics by capturing infrared image data and/or environmental sensor data known to correspond to a particular type of phase transition (e.g., as indicated by a user through manipulation of a user interface, for example). In one embodiment, similar training may be used to select a set of surface characteristics for an imaged surface, for example, or to interpolate between sets of surface characteristics to parameterize an unknown surface. In other embodiments, logic device 110 may perform various image processing operations and image analytics on infrared images of scene 130 to obtain temperature distributions and variance profiles of scene 130 with respect to a variety of environmental conditions. Logic device 110 may use the obtained profiles (e.g., without user input) to select a set of surface characteristics.

In related embodiments, logic device 110 may be adapted to use detected transient characteristics of phase transitions of water to estimate or determine various surface characteristics, as described herein, using one or more pattern recognition operations, interpolation operations, and/or other processing operations. For example, system 100 may be adapted to estimate or determine a thermal conductivity, the constituent material, and/or a temperature of an imaged surface based on detected transient characteristics of a phase transition of water occurring on the surface.

In addition to the above, logic device 110 may be configured to convert infrared images into user-viewable images (e.g., thermograms) using appropriate methods and algorithms. For example, thermographic data contained in infrared images may be converted into gray-scaled or color-scaled pixels to construct images that can be viewed on a display and/or user interface (e.g., a user interface of a remote mitigation or notification system). Such conversion may include adjusting a dynamic range of one or more components of the user-viewable images to match a dynamic range of a particular display or interface, for example, to emphasize a particular radiometric interval, and/or to increase a perceived contrast of user-viewable images. User-viewable images may optionally include a legend or scale that indicates the approximate temperature of a corresponding pixel color and/or intensity, for example, in addition to reporting various aspects of detected phase transitions of water.

Memory 112 may include one or more memory devices (e.g., memory components) to store information, including image and/or video data, other types of sensor data, and/or software instructions. The memory devices may include various types of volatile and non-volatile information storage devices, such as RAM (Random Access Memory), ROM (Read-Only Memory), EEPROM (Electrically-Erasable Read-Only Memory), flash memory, a disk drive, and/or other types of memory. In one embodiment, memory 112 may include a portable memory device that can be removed from system 100 and used to convey stored data to other systems for further processing and inspection. In some embodiments, logic device 110 may be configured to execute software instructions stored on memory 112 to perform various methods, processes, or operations in the manner described herein.

Communication module 114 may be configured to facilitate communication and interfacing between various components of system 100 (e.g., between logic device 110 and display 116) and/or various external networked devices, such as a wireless access point, a personal electronic device, and/or a server. For example, components such as infrared imaging module 102 and other components 118 may transmit and receive data to and from logic device 110 through communication module 114, which may be adapted to manage wired and/or wireless communication links between the various components. Communication module 114 may also be integrated into or implemented as part of various other components of system 100. For example, infrared imaging module 102 and logic device 110 may each comprise a subcomponent that may be configured to perform the operations of communication module 114, and may communicate with one another via wired and/or wireless connections without a separate communication module 114.

In some embodiments, communication module 114 may be configured to allow components of system 100 to communicate and interface with each other as well as other components of other systems associated with scene 130. For example, logic device 110 may communicate, via communication module 114, with a user interface, an ice mitigation system, a notification system, or other detection systems to aggregate reports from multiple systems or sensors and/or implement a particular mitigation or notification method associated with scene 130. In this regard, communication module 114 may support various interfaces, protocols, and standards for local system networking, such as the controller area network (CAN) bus, the local interconnect network (LIN) bus, the media oriented systems transport (MOST) network, or the ISO 11738 (or ISO bus) standard.

In other embodiments, system 100 may include a number of communication modules 118 adapted for various applications of system 100 with respect to different scenes and different types of scenes and corresponding different mitigation and notification systems. For example, communication module 114 may include a wireless communication component (e.g., based on the IEEE 802.11 WiFi standards, the Bluetooth™ standard, the ZigBee™ standard, or other appropriate short range wireless communication standards), a wireless broadband component (e.g., based on WiMax technologies), mobile cellular component, a wireless satellite component, or other appropriate wireless communication components. Communication module 114 may also be configured for a proprietary or secure wireless communication protocol and interface based on radio frequency (RF), microwave frequency (MWF), infrared frequency (IRF), and/or other appropriate wireless transmission technologies. Communication module 114 may include an antenna coupled thereto for wireless communication purposes. Thus, in one embodiment, communication module 114 may be adapted to manage or otherwise facilitate wireless communication by establishing wireless communication links to a wireless router, hub, or other appropriate wireless devices.

Communication module 114 may also be configured to interface with a wired network and/or device via a wired communication component such as an Ethernet interface, a power-line modem, a Digital Subscriber Line (DSL) modem, a Public Switched Telephone Network (PSTN) modem, a cable modem, and/or other appropriate components for wired communication. Proprietary or secure wired communication protocols and interfaces may also be supported by communication module 114. Communication module 114 may be configured to establish and communicate over wired communication links to remote devices and/or systems (e.g., through a network router, switch, hub, or other network devices). For example, a wired communication link may be implemented over a power-line cable, a coaxial cable, a fiber-optic cable, or other appropriate cables or wires that support corresponding wired network technologies.

Display 116 may be configured to present, indicate, or otherwise convey alerts, notifications, infrared images and/or other reports of detection of one or more phase transitions of water in scene 130 (e.g., generated by logic device 110). In one embodiment, display 116 may be implemented with various lighted icons, symbols, and/or indicators. The lighted icons, symbols, and/or indicators may indicate detection of a phase transition of water, a type of detected phase transition of water, and/or a position of a detected phase transition of water in scene 130. The lighted icons, symbols, and/or indicators may also be complemented with an alphanumeric display panel (e.g., a segmented LED panel) to display letters and numbers representing other information, such as various environmental conditions associated with a particular report.

In other embodiments, display 116 may be implemented with an electronic display screen, such as a liquid crystal display (LCD), a cathode ray tube (CRT), or various other types of generally known video displays and monitors, including touch-sensitive displays. Display 116 may be suitable for presenting user-viewable infrared images retrieved and/or generated by processor 110 from images captured by infrared imaging module 102. Moreover, display 116 may be suitable for presenting reports including image overlays indicating a position of a detected phase transition of water in one or more displayed infrared images of scene 130.

Other components 118 may include, in some embodiments, environmental sensors such as a temperature sensor (e.g., a thermocouple, an infrared thermometer), a moisture sensor, a humidity sensor, an atmospheric pressure sensor, an accelerometer, and/or other types of environmental sensors adapted to measure environmental conditions associated with scene 130. Sensor data from such sensors may be utilized by logic device 110 to detect and potentially compensate for environmental conditions when detecting phase transitions of water in scene 130, and thereby produce more reliable reports of detecting such phase transitions.

Other components 118 may also include one or more user interfaces implemented as one or more buttons, indicators (e.g., LEDs), keyboards, trackballs, knobs, joysticks, displays (e.g., a liquid crystal display, a touch-screen display), and/or other type of user interface adapted to accept user input and/or provide user feedback. In one embodiment, a user interface may include a power button, an LED to indicate formation of ice on a nearby walkway or other surface, and/or a joystick to aim or focus infrared imaging module 102 on a particular portion of scene 130. In various embodiments, a user interface may be used to input a variety of system configuration settings, such as expected environmental conditions, as described herein. In some embodiments, a user interface may be used to view one or more reports, infrared images, and/or other sensor data captured by system 100 and/or processed according to the various operations described herein.

Other components 118 may additionally include a power module implemented as a battery, a power adapter, a charging circuit, a power interface, a power monitor, and/or other type of power supply providing a stationary or mobile power source. In some embodiments, the power module may be adapted to provide uninterruptible power and/or power conditioning to protect continued operation of system 100.

Other components 118 may, in some embodiments, include a laser module, for example, or any other device adapted to illuminate all or a portion of scene 130. In various embodiments, the laser module may be tuned to a particular infrared wavelength that is absorbed and/or reflected by water and results in phase transition transient characteristics corresponding to a particular type of phase transition, a particular type or textured surface, and/or other environmental conditions. In other embodiments, the laser module may be tunable (e.g., by logic device 110) across a band of infrared wavelengths. In still further embodiments, other components 118 may include a number of laser modules adapted to more fully illuminate all or portions of scene 130, or to illuminate all or portions of scene 130 in a number of different wavelengths substantially simultaneously, for example. In one embodiment, logic device 110 may be adapted to use one or more such laser modules to illuminate scene 130 when capturing at least one of a series of infrared images of scene 130.

As is also shown in FIG. 1, system 100 may optionally include visible spectrum imaging module 104 and corresponding optional optical elements 105, which may be used to image scene 130 substantially simultaneously with infrared imaging module 102, for example. In various embodiments, visible spectrum imaging module 104 may be implemented as any type of visible spectrum camera or imaging device capable of imaging at least a portion of scene 130 in the visible spectrum. In some embodiments, visible spectrum imaging module 104 may be a small form factor visible spectrum camera or imaging device, and may include one or more logic devices to process and/or store visible spectrum images. Visible spectrum imaging module 104 may be implemented with a charge-coupled device (CCD) sensor, an electron multiplying CCD (EMCCD) sensor, a complementary metal-oxide-semiconductor (CMOS) sensor, a scientific CMOS (sCMOS) sensor, and/or other visible spectrum sensors. Visible spectrum imaging module 104 may include an FPA of visible spectrum sensors, for example, and may be configured to capture, process, and/or manage visible spectrum images of scene 130. Visible spectrum imaging module 104 may be configured to store and/or transmit captured visible spectrum images according to a variety of different color spaces/formats, such as YCbCr, RGB, and YUV, for example, and individual visible spectrum images may be color corrected and/or calibrated according to their designated color space and/or particular characteristics of visible spectrum imaging module 104.

In embodiments of system 100 that include visible spectrum imaging module 104, logic device 110 may be adapted to superimpose, fuse, or otherwise combine visible spectrum image data captured by visible spectrum imaging module 104 with infrared image data captured by infrared imaging module 102 to generate combined images including both infrared and visible spectrum characteristics of scene 130 and thereby provide images of scene 130 with increased object detail, contrast, and other improved or targeted image characteristics. Any of the various phase transition detection methods and processes described herein may be performed using such combined images in addition to or as an alternative to being performed solely with infrared images. Various systems, image analytics, and processing techniques used to produce such combined images are provided in U.S. Provisional Patent Application No. 61/793,952, which is incorporated by reference above.

FIG. 2 illustrates a block diagram of detection system 200 in accordance with an embodiment of the disclosure. As shown in FIG. 2, detection system 200 may be a distributed form of detection system 100, for example, including system 100 in communication with server 208 and various personal electronic devices, such as mobile device 204 and/or personal computer 206 over one or more communication links and/or network 202.

In one embodiment, mobile device 204 and/or personal computer 206 may be adapted to present a user interface for a remote mitigation and/or notification system to one or more users of mobile device 204 and/or personal computer 206. Such user interface may be adapted to display infrared images and/or reports generated and transmitted by system 100, and may be adapted to accept user input through use of a touch screen interface, a keyboard, a mouse, and/or other type of conventional user interface device, for example, as described herein. Mobile device 204 may be implemented as a mobile phone, smartphone, tablet computer, vehicle computers, and/or other mobile personal electronic device. Personal computer 208 may be implemented as a desktop computer, a fixed terminal device, a network enabled television, a home entertainment center, and/or other relatively stationary personal electronic device.

In some embodiments, network 202 may represent a WAN, LAN, and/or other network and/or combination of networks, including the Internet, and monitoring system 100 may be adapted to establish communication links with the various personal electronic devices directly through network 202 and/or indirectly through server 208. In other embodiments, network 202 and the various communication links may represent an ad-hoc wireless and/or wired network, a proprietary network, and/or a mixed network, and monitoring system 100 may be adapted to establish a variety of types of communication links with the various devices of system 200.

In various embodiments, server 208 may be a host or other type of networked computer or distributed group of networked computers implemented as at least part of a mitigation and/or notification system. For example, server 208 may include various mitigation components, such as heaters, ultrasonic transducers, and/or other components adapted to remove or reduce ice, for example, and/or components adapted to remove or reduce accumulation of liquid water. In some embodiments, server 208 may be adapted to receive a report of phase transitions of water from system 100 and then selectively modulate operation of one or more mitigation systems to reduce or eliminate safety hazards or other negative consequences of accumulation of liquid water and/or ice, as described herein. In other embodiments, server 208 may be adapted to distribute one or more notifications of reports transmitted by system 100 to other devices (e.g., mobile device 204 and/or personal computer 206) and/or users, for example, such as devices or users associated with scene 130.

In additional embodiments, server 208 may be a host or other type of networked computer or distributed group of networked computers implemented as a value-added and/or pay-for service provider requiring registration and/or subscription before access is granted (e.g., before a communication link is allowed) to and/or among monitoring system 100, mobile device 204, and/or personal computer 206. Server 208 may be implemented as an intermediary between monitoring system 100 and the various personal electronic devices, for example, and may adapted to manage and/or store one or more user and/or device specific databases including various types images, reports, and/or other data described herein.

FIGS. 3A-3C depict a series of infrared images illustrating transient characteristics of the formation of ice on a rubber surface in accordance with an embodiment of the disclosure. Infrared image 310 of FIG. 3A was captured approximately 2 seconds after rubber surface 301 was sprayed with water 302. Infrared image 320 of FIG. 3B was captured approximately 4 seconds after rubber surface 301 was sprayed with water, and distinctive pattern 303 of ice formation on rubber surface 301 has formed and grown relatively bright. Infrared image 330 of FIG. 3C was captured approximately 15 seconds after rubber surface 301 was sprayed with water, and distinctive pattern 303 of ice formation on rubber surface 301 has grown relatively dim.

Figure 4A:
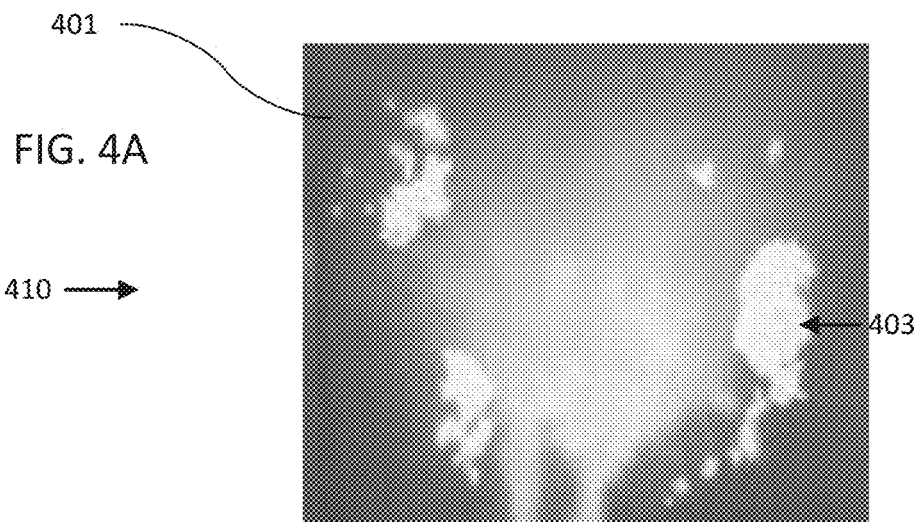
FIGS. 4A-4B depict a series of infrared images illustrating transient characteristics of the formation of ice on a wooden surface in accordance with an embodiment of the disclosure.
Figure 4B:
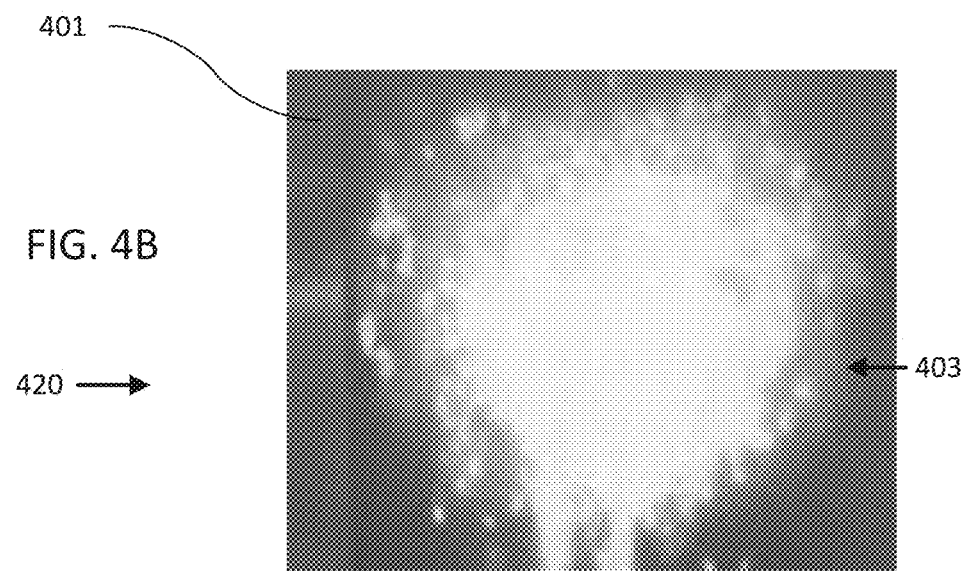

FIGS. 4A-4B depict a series of infrared images illustrating transient characteristics of the formation of ice on a wooden surface in accordance with an embodiment of the disclosure, for comparison with FIGS. 3A-3C. Infrared image 410 of FIG. 4A was captured approximately 3 seconds after wooden surface 401 was sprayed with water, and distinctive pattern 403 of ice formation on wooden surface 401 has begun to form and grow bright. Infrared image 420 of FIG. 4B was captured approximately 15 seconds after wooden surface 401 was sprayed with water, and distinctive pattern 403 of ice formation on rubber surface 301 has grown larger and continues to be relatively bright.

Figure 5:
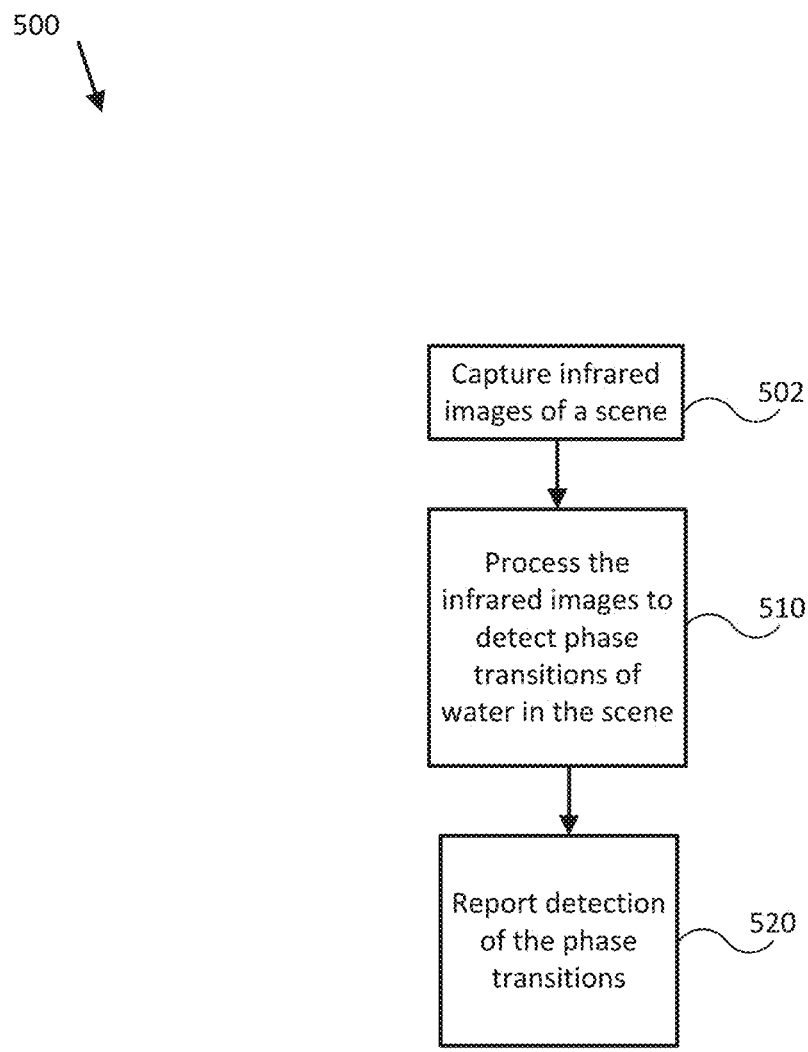
FIG. 5 illustrates a flow diagram of various operations to provide phase transition detection and reporting in accordance with an embodiment of the disclosure.

FIG. 5 illustrates a flow diagram of process 500 to provide phase transition detection in accordance with an embodiment of the disclosure. In some embodiments, the operations of FIG. 5 may be implemented as software instructions executed by one or more logic devices used to implement a detection system. More generally, the operations of FIG. 5 may be implemented with any combination of software instructions, electronic hardware (e.g., inductors, capacitors, amplifiers, or other analog and/or digital components), and/or mechanical hardware used with a detection system. It should be appreciated that any step, sub-step, sub-process, or block of process 500 may be performed in an order or arrangement different from the embodiment illustrated by FIG. 5. Further, in some embodiments, any number of processes similar to process 500 may be performed substantially simultaneously to produce multiple instances of phase transition detection throughout a distributed detection system, for example. Although process 500 is described with reference to systems 100 and 200, process 500 may be performed according to systems different from systems 100 or 200 and including a different selection and/or number of modules and/or components.

In block 502, a phase transition detection process includes capturing infrared images of a scene. For example, logic device 110 of system 100 may be adapted to use infrared imaging module 102 and optical elements 103 to capture one or more infrared images of scene 130. In some embodiments, logic device 110 may be adapted to capture a series of infrared images with a common FOV. In other embodiments, logic device 110 may be adapted to capture infrared images with different but overlapping FOVs so as to capture multiple portions of scene 130 over time.

In block 510, a phase transition detection process includes processing the infrared images captured in block 502 to detect phase transitions of water in the imaged scene. For example, logic device 110 of system 100 may be adapted to process infrared images of scene 130 to detect one or more phase transitions of water in scene 130. In one embodiment, logic device 110 may be adapted to apply any of the image and/or signal processing techniques described herein to the infrared images captured in block 510. In another embodiment, logic device 110 may be adapted to detect one or more phase transitions by generating a list of targets from a single infrared image and eliminating false-positive targets with non-conforming amplitudes or spatial patterns. In a further embodiment, logic device 110 may be adapted to detect phase transitions by generating a list of targets from a series of infrared images with a common FOV and eliminating false-positive targets with non-conforming transient characteristics. In a still further embodiment, logic device 110 may be adapted to detect phase transitions by generating a list of targets from a series of infrared images with different but overlapping FOVs and eliminating false-positive targets with non-conforming transient characteristics. In some embodiments, logic device 110 may be adapted to register targets in multiple images before creating the target list.

In block 520, a phase transition detection process includes reporting the phase transitions detected in block 510. For example, logic device 110 of system 100 may be adapted to report detections of phase transitions of water in scene 130 using communication module 113. In one embodiment, logic device 110 may be adapted to report detections of phase transitions by energizing/de-energizing an indicator and/or transmitting one or more signals to a component of system 100 or to an external system or device. In another embodiment, logic device 110 may be adapted to report detections of phase transitions by generating an image overlay indicating type and/or position of a phase transition and transmitting the image overlay and a corresponding infrared image to display 116 for simultaneous display. In a further embodiment, an external system or device receiving a report may be implemented as a mitigation and/or notification system, for example, and be adapted to mitigate or take advantage of the reported detection by modulating a mitigation device and/or a notification device according to the timing and type of reported detection.

Figure 6:
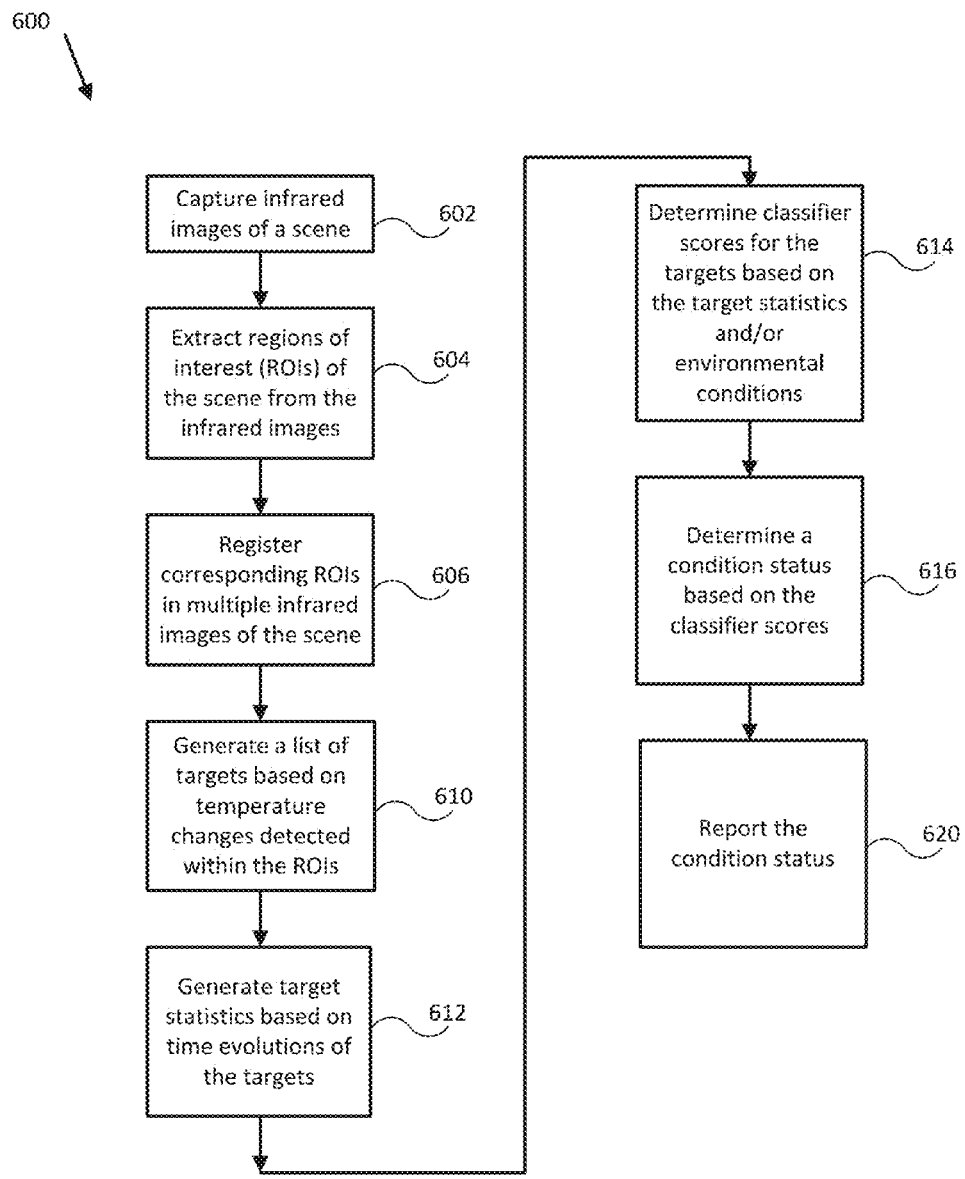
FIG. 6 illustrates a flow diagram of various operations to provide phase transition detection and reporting in accordance with an embodiment of the disclosure.

FIG. 6 illustrates a flow diagram of process 600 to provide phase transition detection in accordance with an embodiment of the disclosure. In some embodiments, the operations of FIG. 6 may be implemented as software instructions executed by one or more logic devices used to implement a detection system. More generally, the operations of FIG. 6 may be implemented with any combination of software instructions, electronic hardware, and/or mechanical hardware used with a detection system. Any step, sub-step, sub-process, or block of process 600 may be performed in an order or arrangement different from the embodiment illustrated by FIG. 6. Further, in some embodiments, any number of processes similar to process 600 may be performed substantially simultaneously to produce multiple instances of phase transition detection throughout a distributed detection system, for example. Although process 600 is described with reference to systems 100 and 200, process 600 may be performed according to systems different from systems 100 or 200 and including a different selection and/or number of modules and/or components.

In block 602, a phase transition detection process includes capturing infrared images of a scene. For example, logic device 110 of system 100 may be adapted to use infrared imaging module 102 and optical elements 103 to capture one or more infrared images of scene 130. In some embodiments, logic device 110 may be adapted to capture a series of infrared images with a common FOV. In other embodiments, logic device 110 may be adapted to capture infrared images with different but overlapping FOVs so as to capture multiple portions of scene 130 over time. Where infrared images include both static and dynamic content, a common or overlapping FOV may be in relation to static portions of the infrared images.

In block 604, a phase transition detection process includes extracting one or more regions of interest (ROIs) of the scene from the infrared images captured in block 602. For example, logic device 110 of system 100 may be adapted to process one or more infrared images of scene 130 to segregate a group of spatially and/or temporally adjoining pixels from the remaining pixels of the one or more infrared images to form a corresponding ROI. The shape and/or extents of the one or more ROIs may correspond to a particular surface or portion of a surface in scene 130, for example, and/or may correspond to a particular region or perspective of a region of scene 130. In one embodiment, a ROI may correspond to a portion of scene 130 particularly susceptible to negative repercussions associated with a particular type of phase transition of water. For example, a ROI may correspond to a shaded portion of roadway 136 that is particularly susceptible to formation of black ice.

In some embodiments, one or more ROIs may be defined, at least in part, by user input, for example, or may be specified at manufacture. In other embodiments, one or more ROIs may be defined, at least in part, through historical profiling of scene 130 to determine areas most susceptible to phase transitions of water for particular set of environmental conditions. In further embodiments, one or more ROIs may be defined, at least in part, by operation of one or more pattern recognition routines to detect a particular surface or surface characteristic, motion of an object within scene 130, and/or one or more combinations of environmental conditions (e.g., type of precipitation, orientation relative to the sun), for example. In some embodiments, ROIs may be defined by any combination of the above. Extracted ROIs may be stored separately in memory 113, for example, or may be stored within their originating images as pixels with an additional identifier segregating them from other pixels and other ROIs.

In block 606, a phase transition detection process includes registering corresponding ROIs in multiple infrared images of scene 130. For example, logic device 110 may be adapted to process one or more infrared images of scene 130 to align (e.g., through image translation, scaling, and/or rotation transformations) different perspectives of the same ROI as presented in subsequent images. For example, where captured infrared images have common FOVs, registering substantially static ROIs would typically not be necessary, but registering dynamic ROIs (e.g., a particular surface or region of scene 130 in motion relative to infrared imaging module 102) would likely require application of one or more translation, scaling, or rotation transformations to at least the ROI portion of the infrared image. In embodiments where the infrared images include static and dynamic ROIs, non-ROI portions of the infrared imaged may be warped and/or eliminated to allow for registration with minimal distortion of the ROIs themselves. In various embodiments, different perspectives of the same ROI may be aligned to within one half of a pixel diameter across the extents of the ROI boundary.

In block 610, a phase transition detection process includes generating a list of targets based on temperature and/or intensity changes detected within the ROIs registered in block 606. For example, logic device 110 may be adapted to processes one or more captured infrared images of scene 130 to generate a list of targets (e.g., a list of pixels or substantially adjoining groups of pixels) indicating a temporal temperature/intensity difference (e.g., a change in infrared radiation from image to image in a time series of infrared images) within registered ROIs. In some embodiments, logic device 110 may additionally or alternatively be adapted to generate a list of targets indicating a spatial temperature/intensity difference (e.g., a change in infrared radiation from target to non-target in a single image), for example, or a list of targets indicating a spatial or temporal temperature/intensity difference, as described herein. In one embodiment, detecting spatial or temporal temperature/intensity differences in an ROI and/or designating pixels as targets may include comparing a pixel to one or more layers of its spatial and/or temporal neighbors, calculating a difference between a pixel value and corresponding values in the one or more layers, comparing the results of the subtractions, and/or other image processing and/or segmentation operations.

In block 612, a phase transition detection process includes generating target statistics based on time evolutions of the targets listed in block 610. For example, logic device 110 may be adapted to process portions of a time series of infrared images corresponding to the targets listed in block 610 to generate target statistics associated with each of the targets listed in block 610. In one embodiment, various target statistics may correspond to one or more transient characteristics, such as an amplitudes, time evolutions, spatial patterns, and/or other transient characteristics associated with a target, as described herein. For example, a target statistic may include a historical log of the amplitude of a detected temperature/intensity change associated with a particular target.

In block 614, a phase transition detection process includes determining classifier scores for the targets listed in block 610 based on the target statistics generated in block 612 and/or various environmental conditions. For example, logic device 110 may be adapted to determine classifier scores (e.g., numerical values) associated with each listed target based on an analysis of the target statistics and/or sensed or expected environmental conditions, as described herein. In various embodiments, the classifier scores may be selected to reflect an estimated likelihood that its associated target is a detected phase transition of water, for example, and/or to reflect the type of detected phase transition of water. Any of a variety of classifier score assignment schemes is contemplated.

For example, in one embodiment, logic device 110 may be adapted to assign a relatively high positive or negative classifier score to a particular target if its associated target statistics conform to expected transient characteristics for a liquid water to ice phase transition (e.g., a positive classifier score) or an ice to liquid water phase transition (e.g., a negative classifier score), where the expected transient characteristics may be varied (e.g., by logic device 110) according to sensed and/or expected environmental conditions.

In some embodiments, logic device 110 may be adapted to remove a target from the list generated in block 610 if its classifier score indicates low likelihood of a phase transition of water. For example, in the embodiment described above, logic device 110 may be adapted to remove a target from the list if the absolute value of its classifier score is less than a user defined threshold (e.g., neither high enough or low enough to indicate a detected phase transition of water), for example, or less than a threshold at least partially derived from a set of classifier scores associated with the listed targets (e.g., a threshold range selected to remove the ten percent of targets with classifier scores closest to zero).

In block 616, a phase transition detection process includes determining a condition status based on the classifier scores determined in block 614. For example, logic device 110 may be adapted to determine a condition status (e.g., an indication of a detection of one or more phase transitions of water, and/or an indication of the type of detected phase transitions) of scene 130 and/or one or more of the ROIs extracted and registered in blocks 604 and 606, based on the classifier scores determined in block 614 for each of the targets listed in block 610. Any of a variety of condition status assignment schemes is contemplated.

For example, in one embodiment, a condition status may correspond to an aggregation of positive (or negative) classification scores associated with a particular ROI over a particular time period. Logic device 110 may be adapted to sum all positive or all negative classifier scores for targets within an ROI and assign a value to the corresponding condition status indicating, for example, the number of targets with classifier scores above a user defined or statistically derived threshold (e.g., the estimated number of detected phase transitions) and/or the type of phase transitions detected. The aggregation time period may be user defined, for example, or may vary according to one or more environmental conditions or other measured or derived characteristics of scene 130 or a particular ROI.

In block 620, a phase transition detection process includes reporting the condition status determined in block 616. For example, logic device 110 of system 100 may be adapted to report a condition status of scene 130 using communication module 113. In one embodiment, logic device 110 may be adapted to report a condition status by energizing/de-energizing an indicator and/or transmitting one or more signals to a component of system 100 or to an external system or device. In another embodiment, logic device 110 may be adapted to report a condition status by generating an image overlay indicating type of status (e.g., type of detected phase transition) and/or shape or position of one or more associated ROIs, and then transmitting the image overlay and a corresponding infrared image to display 116 for simultaneous display. In a further embodiment, an external system or device receiving a report may be implemented as a mitigation and/or notification system, for example, and be adapted to mitigate or take advantage of the reported condition status by modulating a mitigation device according to the timing and type of reported condition status.

Figure 7:
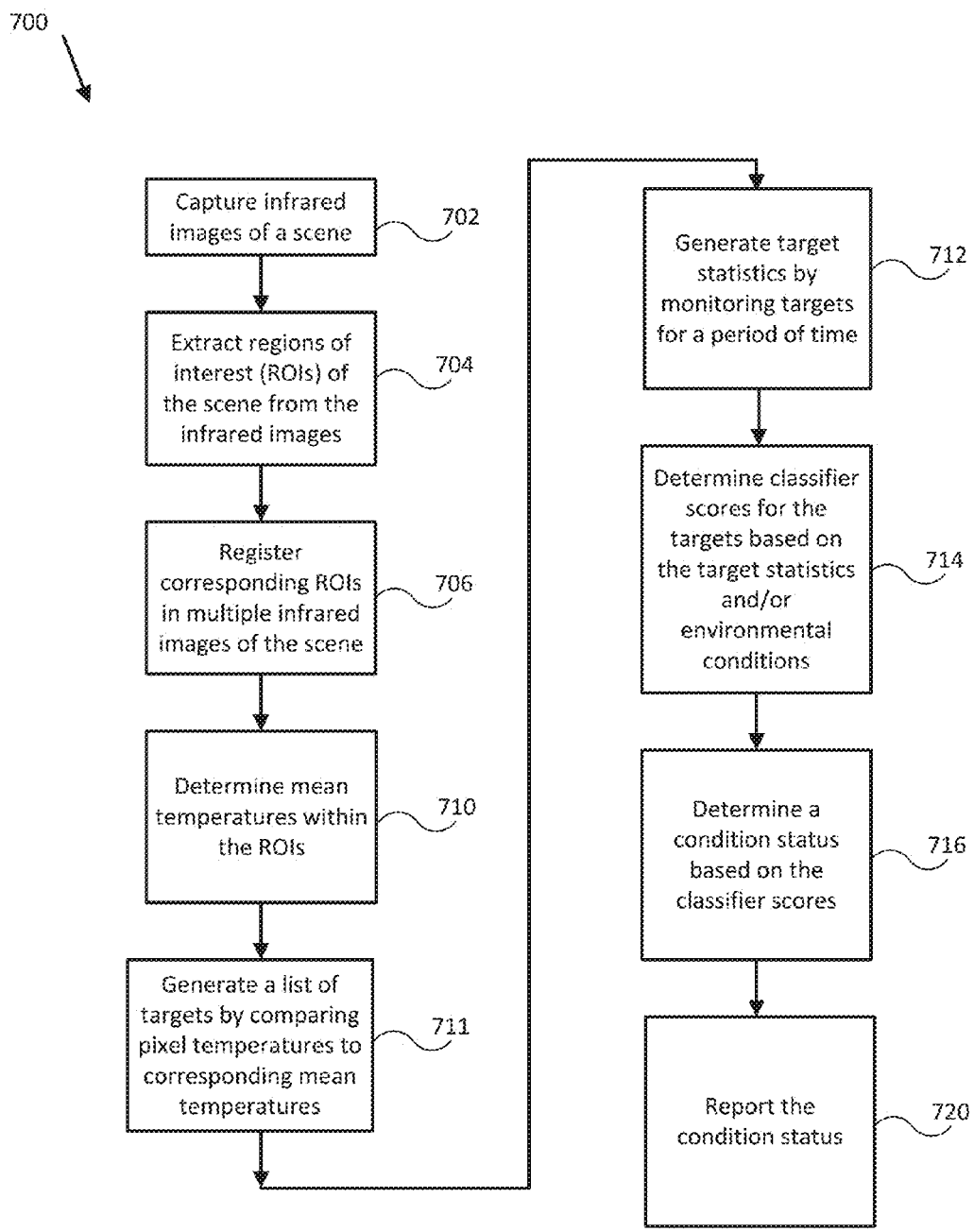
FIG. 7 illustrates a flow diagram of various operations to provide phase transition detection and reporting in accordance with an embodiment of the disclosure.

FIG. 7 illustrates a flow diagram of process 700 to provide phase transition detection in accordance with an embodiment of the disclosure. In some embodiments, the operations of FIG. 7 may be implemented as software instructions executed by one or more logic devices used to implement a detection system. More generally, the operations of FIG. 7 may be implemented with any combination of software instructions, electronic hardware, and/or mechanical hardware used with a detection system. Any step, sub-step, sub-process, or block of process 700 may be performed in an order or arrangement different from the embodiment illustrated by FIG. 7. Further, in some embodiments, any number of processes similar to process 700 may be performed substantially simultaneously to produce multiple instances of phase transition detection throughout a distributed detection system, for example Although process 700 is described with reference to systems 100 and 200, process 700 may be performed according to systems different from systems 100 or 200 and including a different selection and/or number of modules and/or components.

In block 702, a phase transition detection process includes capturing infrared images of a scene. For example, logic device 110 of system 100 may be adapted to use infrared imaging module 102 and optical elements 103 to capture one or more infrared images of scene 130. In some embodiments, logic device 110 may be adapted to capture a series of infrared images with a common FOV. In other embodiments, logic device 110 may be adapted to capture infrared images with different but overlapping FOVs so as to capture multiple portions of scene 130 over time. Where infrared images include both static and dynamic content, a common or overlapping FOV may be in relation to static portions of the infrared images.

In block 704, a phase transition detection process includes extracting one or more regions of interest (ROIs) of the scene from the infrared images captured in block 702. For example, logic device 110 of system 100 may be adapted to process one or more infrared images of scene 130 to segregate a group of spatially and/or temporally adjoining pixels from the remaining pixels of the one or more infrared images to form a corresponding ROI. The shape and/or extents of the one or more ROIs may correspond to a particular surface or portion of a surface in scene 130, for example, and/or may correspond to a particular region or perspective of a region of scene 130. In one embodiment, a ROI may correspond to a portion of scene 130 particularly susceptible to negative repercussions associated with a particular type of phase transition of water. For example, a ROI may correspond to a shaded portion of roadway 136 that is particularly susceptible to formation of black ice.

In some embodiments, one or more ROIs may be defined, at least in part, by user input, for example, or may be specified at manufacture. In other embodiments, one or more ROIs may be defined, at least in part, through historical profiling of scene 130 to determine areas most susceptible to phase transitions of water for particular set of environmental conditions. In further embodiments, one or more ROIs may be defined, at least in part, by operation of one or more pattern recognition routines to detect a particular surface or surface characteristic, motion of an object within scene 130, and/or one or more combinations of environmental conditions (e.g., type of precipitation, orientation relative to the sun), for example. In some embodiments, ROIs may be defined by any combination of the above. Extracted ROIs may be stored separately in memory 113, for example, or may be stored within their originating images as pixels with an additional identifier segregating them from other pixels and other ROIs.

In block 706, a phase transition detection process includes registering corresponding ROIs in multiple infrared images of scene 130. For example, logic device 110 may be adapted to process one or more infrared images of scene 130 to align (e.g., through image translation, scaling, and/or rotation transformations) different perspectives of the same ROI as presented in subsequent images. For example, where captured infrared images have common FOVs, registering substantially static ROIs would typically not be necessary, but registering dynamic ROIs (e.g., a particular surface or region of scene 130 in motion relative to infrared imaging module 102) would likely require application of one or more translation, scaling, or rotation transformations to at least the ROI portion of the infrared image. In embodiments where the infrared images include static and dynamic ROIs, non-ROI portions of the infrared imaged may be warped and/or eliminated to allow for registration with minimal distortion of the ROIs themselves. In various embodiments, different perspectives of the same ROI may be aligned to within one half of a pixel diameter across the extents of the ROI boundary.

In block 710, a phase transition detection process includes determining mean temperatures and/or intensities within the ROIs extracted in block 704 and registered in block 706. For example, logic device 110 may be adapted to process one or more registered ROIs of captured infrared images of scene 130 to determine corresponding mean temperatures/intensities within the ROIs. In one example, logic device 110 may be adapted to determine the mean temperature/intensity within an ROI by summing the temperature/intensity values corresponding to each pixel in an ROI and then dividing the total by the number of pixels in the ROI.

In block 711, a phase transition detection process includes generating a list of targets by comparing pixel temperatures and/or intensities to corresponding mean temperatures and/or intensities determined in block 710. For example, logic device 110 may be adapted to process one or more ROIs of captured infrared images of scene 130 to generate a list of targets within each ROI indicating a temperature/intensity greater than a mean temperature/intensity of an associated extracted and/or registered ROI. In such embodiment, the resulting target list may indicate portions of ROIs potentially associated with the formation of ice. In other embodiments, logic device 110 may be adapted to process one or more ROIs to generate a list of targets within each ROI indicating a temperature/intensity less than a mean temperature/intensity of an associated extracted and/or registered ROI. In such embodiment, the resulting target list may indicate portions of ROIs potentially associated with the melting of ice. In some embodiments, both target lists are generated. In one embodiment, designating individual pixels and/or groups of pixels as targets may include comparing a pixel to one or more layers of its spatial and/or temporal neighbors, calculating a difference between a pixel value and corresponding values in the one or more layers, comparing the results of the subtractions, and/or other image processing and/or segmentation operations.

In block 712, a phase transition detection process includes generating target statistics based on time evolutions of the targets listed in block 610 measured over a predetermined period of time. For example, logic device 110 may be adapted to process portions of a time series of infrared images corresponding to the targets listed in block 711 to generate target statistics associated with each of the targets listed in block 711. In one embodiment, various target statistics may correspond to one or more transient characteristics, such as an amplitudes, time evolutions, spatial patterns, and/or other transient characteristics associated with a target, as described herein. For example, a target statistic may include a historical log of the amplitude of a detected temperature or intensity associated with a particular target and/or a shape of a spatial pattern of a particular target at a maximum, minimum, or mean amplitude of detected temperature/intensity associated with the target.

In block 714, a phase transition detection process includes determining classifier scores for the targets listed in block 711 based on the target statistics generated in block 712 and/or various environmental conditions. For example, logic device 110 may be adapted to determine classifier scores (e.g., numerical values) associated with each listed target based on an analysis of the target statistics and/or sensed or expected environmental conditions, as described herein. In various embodiments, the classifier scores may be selected to reflect an estimated likelihood that its associated target is a detected phase transition of water, for example, and/or to reflect the type of detected phase transition of water. Any of a variety of classifier score assignment schemes is contemplated.

For example, in one embodiment, logic device 110 may be adapted to assign a relatively high positive or negative classifier score to a particular target if its associated target statistics conform to expected transient characteristics for a liquid water to ice phase transition (e.g., a positive classifier score) or an ice to liquid water phase transition (e.g., a negative classifier score), where the expected transient characteristics may be varied (e.g., by logic device 110) according to sensed and/or expected environmental conditions.

In some embodiments, logic device 110 may be adapted to remove a target from the list generated in block 711 if its classifier score indicates low likelihood of a phase transition of water. For example, in the embodiment described above, logic device 110 may be adapted to remove a target from the list if the absolute value of its classifier score is less than a user defined threshold (e.g., neither high enough or low enough to indicate a detected phase transition of water), for example, or less than a threshold at least partially derived from a set of classifier scores associated with the listed targets (e.g., a threshold range selected to remove the ten percent of targets with classifier scores closest to zero).

In block 716, a phase transition detection process includes determining a condition status based on the classifier scores determined in block 714. For example, logic device 110 may be adapted to determine a condition status (e.g., an indication of a detection of one or more phase transitions of water, and/or an indication of the type of detected phase transitions) of scene 130 and/or one or more of the ROIs extracted and registered in blocks 704 and 706, based on the classifier scores determined in block 714 for each of the targets listed in block 711. Any of a variety of condition status assignment schemes is contemplated.

For example, in one embodiment, a condition status may correspond to an aggregation of positive (or negative) classification scores associated with a particular ROI over a particular time period. Logic device 110 may be adapted to sum all positive or all negative classifier scores for targets within an ROI and assign a value to the corresponding condition status indicating, for example, the number of targets with classifier scores above a user defined or statistically derived threshold (e.g., the estimated number of detected phase transitions) and/or the type of phase transitions detected. The aggregation time period may be user defined, for example, or may vary according to one or more environmental conditions or other measured or derived characteristics of scene 130 or a particular ROI.

In block 720, a phase transition detection process includes reporting the condition status determined in block 716. For example, logic device 110 of system 100 may be adapted to report a condition status of scene 130 using communication module 113. In one embodiment, logic device 110 may be adapted to report a condition status by energizing/de-energizing an indicator and/or transmitting one or more signals to a component of system 100 or to an external system or device. In another embodiment, logic device 110 may be adapted to report a condition status by generating an image overlay indicating type of status (e.g., type of detected phase transition) and/or shape or position of one or more associated ROIs, and then transmitting the image overlay and a corresponding infrared image to display 116 for simultaneous display. In a further embodiment, an external system or device receiving a report may be implemented as a mitigation and/or notification system, for example, and be adapted to mitigate or take advantage of the reported condition status by modulating a mitigation device according to the timing and type of reported condition status.

Figure 8A:
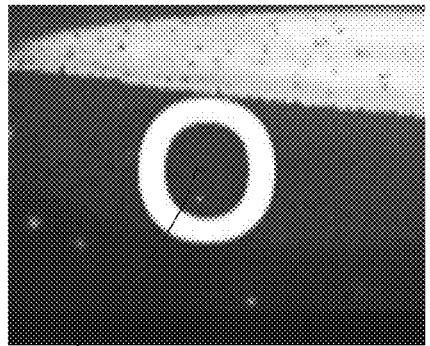
FIGS. 8A-8D depict a series of infrared images illustrating transient characteristics of the formation of ice in accordance with an embodiment of the disclosure.
Figure 8B:
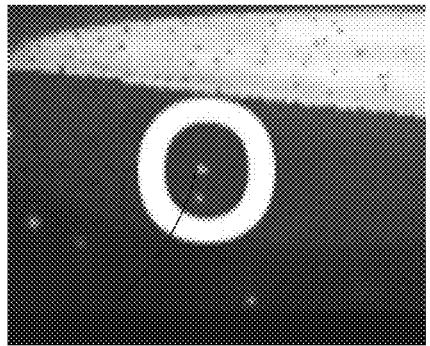
Figure 8C:
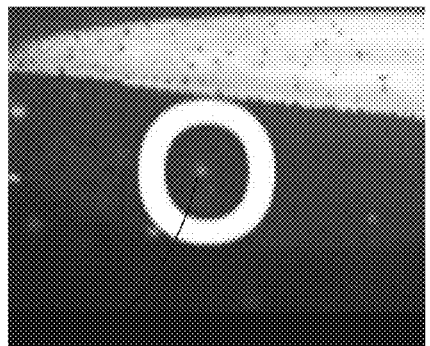
Figure 8D:
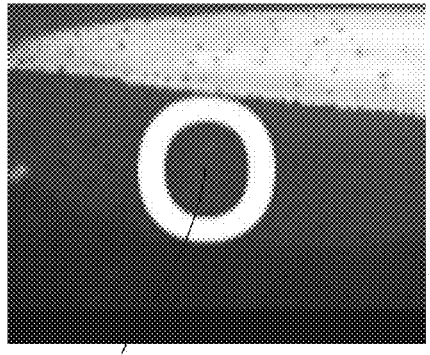

FIGS. 8A-8D depict a series of infrared images illustrating transient characteristics of the formation of ice in accordance with an embodiment of the disclosure. Infrared image 810 of FIG. 8A illustrates a drop 802 of water on a surface before onset of ice formation. Infrared image 820 of FIG. 8B illustrates drop 802 during onset of ice formation, and drop 802 has grown relatively bright. Infrared image 830 of FIG. 8C illustrates drop 802 further along the transient time evolution associated with the onset of ice formation shown in FIG. 8B, and drop 802 has started to dim. Infrared image 840 of FIG. 8D illustrates drop 802 after it has transitioned to ice and after it has dimmed to substantially ambient emission levels. Taken together as a series, it can be seen from FIGS. 8A through 8D that the phase transition from liquid water to ice of drop 802 appears as a "sparkle" of relatively short-lived but detectable intensity in the infrared band.

By providing substantial real time detection of phase transitions of water, including both formation and melting of ice, mitigation and/or notification systems incorporating embodiments of the present disclosure offer substantially increased safety and mitigation efficiency. Furthermore, because embodiments of the present disclosure may be adapted to detect phase transitions of water optically and over multiple large regions substantially simultaneously, the increased safety and mitigation efficiency may be provided by relatively few detection system installations and therefore at a substantially reduced cost relative to conventional detection systems.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:
1. A system comprising:
an infrared imaging module;
a communication module; and
a logic device configured to communicate with the infrared imaging module and the communication module, wherein the logic device is configured to:
capture infrared images of a scene using the infrared imaging module;
process the infrared images; and
detect one or more phase transitions of water in the processed infrared images of the scene by generating a list of targets from the infrared images and eliminating false-positive targets in the list having one or more non-conforming transient characteristics in the infrared images of the scene.
2. The system of claim 1, wherein the logic device is configured to:
capture a series of infrared images having a common field of view (FOV) or different but overlapping FOVs;
detect the one or more phase transitions of water by generating the list of targets from the infrared images, wherein each target in the list of targets corresponds to transient characteristics of the one or more phase transitions detected in the infrared images of the scene that occur during the one or more detected phase transitions of water;
and
report the detection of the one or more phase transitions using the communication module.
3. The system of claim 2, further comprising a mitigation and/or notification system, wherein:
the logic device is configured to report the detection of the one or more phase transitions by generating an image overlay indicating type and/or position of the one or more phase transitions and transmitting the image overlay and a corresponding infrared image to a display; and
the mitigation and/or notification system is configured to receive the reported detection of the one or more phase transitions and modulate one or more signals provided to a mitigation device and/or a notification device according to a timing and type of reported detection.
4. The system of claim 1, wherein the logic device is configured to:

extract one or more regions of interest (ROIs) of the scene from at least one of the infrared images;
register corresponding ROIs in the at least one of the infrared images; and
detect the one or more phase transitions of water in the one or more ROIs.

5. The system of claim 1, wherein the logic device is configured to detect the one or more phase transitions of water in the scene by:
generating the list of targets based on intensity changes detected within the infrared images;
generating target statistics based on time evolutions of the targets in the list;
determining classifier scores for the targets in the list based on the target statistics; and
determining a condition status of the scene based on the classifier scores.

6. The system of claim 1, wherein the logic device is configured to detect the one or more phase transitions of water in the scene by:
extracting a region of interest (ROI) of the scene from at least one of the infrared images;
determining a mean intensity within the ROI;
generating the list of targets by comparing pixel intensities within the ROI to the mean intensity;
generating target statistics based on time evolutions of the targets in the list measured over a predetermined period of time;
determining classifier scores for the targets in the list based on the target statistics; and
determining a condition status of the scene based on the classifier scores.

7. The system of claim 1, further comprising a visible spectrum imaging module in communication with the logic device, wherein the logic device is configured to:
capture visible spectrum images of the scene using the visible spectrum imaging module;
generate combined images comprising visible spectrum image data and infrared image data, wherein the combined images provide increased object detail, contrast, and/or other improved or targeted image characteristics, and wherein the reporting the detection of the one or more phase transitions comprises transmitting at least one of the combined images.

8. The system of claim 1, further comprising a laser module configured to communicate with the logic device, wherein:
the infrared imaging module is configured to image near-infrared radiation (NIR), short wavelength infrared radiation (SWIR), mid-wavelength infrared radiation (MWIR), long-wavelength infrared radiation (LWIR), far-infrared radiation (FIR), and/or multispectral infrared radiation; and
the logic device is configured to illuminate at least a portion of the scene using the laser module when capturing at least one of the infrared images and/or to apply a dynamic range adjustment filter and/or a bandpass filter when capturing the infrared images and/or processing the captured infrared images.

9. The system of claim 1, wherein:
the scene comprises a marker surface configured to provide detectable transient characteristics associated with the one or more phase transitions of water in a corresponding portion of the scene; and
the detectable transient characteristics associated with the one or more phase transitions of water each comprise a time evolution comprising an onset, saturation, and decay that occurs during the one or more detected phase transitions and takes place over a time period ranging from less than a second to approximately 20 seconds.

10. The system of claim 1, wherein:
the scene comprises a surface, wherein at least of the detected one or more phase transitions of water is located on the surface;
the method further comprises estimating a thermal conductivity, a constituent material, and/or a temperature of the surface based on the at least one of the detected one or more phase transitions of water; and
the scene comprises a roadway, a walkway, an automobile surface, an aircraft surface, a propeller surface, a combustion engine intake, and/or a crop surface.

11. A method comprising:
capturing infrared images of a scene using an infrared imaging module;
processing the infrared images; and
detecting one or more phase transitions of water in the processed infrared images of the scene by generating a list of targets from the infrared images, wherein each target in the list of targets corresponds to transient characteristics of the one or more phase transitions detected in the infrared images of the scene that occur during the one or more detected phase transitions of water.

12. The method of claim 11, further comprising:
capturing a series of infrared images having a common field of view (FOV) or different but overlapping FOVs;
detecting the one or more phase transitions of water by generating the list of targets from the series of infrared images;
eliminating false-positive targets in the list having one or more non-conforming transient characteristics; and
reporting the detection of the one or more phase transitions using a communication module.

13. The method of claim 12, further comprising:
reporting the detection of the one or more phase transitions by generating an image overlay indicating type and/or position of the one or more phase transitions and transmitting the image overlay and a corresponding infrared image to a display;
receiving, by a mitigation and/or notification system, the reported detection of the one or more phase transitions; and
modulating one or more signals provided to a mitigation device and/or a notification device according to a timing and type of reported detection.

14. The method of claim 11, further comprising:
extracting one or more regions of interest (ROIs) of the scene from at least one of the infrared images;
registering corresponding ROIs in the plurality of the infrared images; and
detecting the one or more phase transitions of water in the one or more ROIs.

15. The method of claim 11, wherein the detecting the one or more phase transitions of water in the scene comprises:
generating the list of targets based on intensity changes detected within the infrared images;
generating target statistics based on time evolutions of the targets in the list;
determining classifier scores for the targets in the list based on the target statistics; and
determining a condition status of the scene based on the classifier scores.

16. The method of claim 11, wherein the logic device is configured to detect the one or more phase transitions of water in the scene by:
- extracting a region of interest (ROI) of the scene from at least one of the infrared images;
- determining a mean intensity within the ROI;
- generating the list of targets by comparing pixel intensities within the ROI to the mean intensity;
- generating target statistics based on time evolutions of the targets in the list measured over a predetermined period of time;
- determining classifier scores for the targets in the list based on the target statistics; and
- determining a condition status of the scene based on the classifier scores.

17. The method of claim 11, further comprising:
- capturing visible spectrum images of the scene using a visible spectrum imaging module; and
- generating combined images comprising visible spectrum image data and infrared image data, wherein the combined images provide increased object detail, contrast, and/or other improved or targeted image characteristics, and wherein the reporting the detection of the one or more phase transitions comprises transmitting at least one of the combined images.

18. The method of claim 11, wherein the infrared imaging module is configured to image near-infrared radiation (NIR), short wavelength infrared radiation (SWIR), mid-wavelength infrared radiation (MWIR), long-wavelength infrared radiation (LWIR), far-infrared radiation (FIR), and/or multi-spectral infrared radiation, and wherein the method further comprises:
- applying a dynamic range adjustment filter and/or a bandpass filter when capturing the infrared images and/or processing the captured infrared images; and/or
- illuminating at least a portion of the scene with a laser module when capturing at least one of the infrared images.

19. The method of claim 11, wherein:
- the scene comprises a marker surface configured to provide detectable transient characteristics associated with the one or more phase transitions of water in a corresponding portion of the scene; and
- the detectable transient characteristics associated with the one or more phase transitions of water each comprise a time evolution comprising an onset, saturation, and decay that occurs during the one or more detected phase transitions and takes place over a time period ranging from less than a second to approximately 20 seconds.

20. The method of claim 11, wherein:
- the scene comprises a surface, wherein at least of the detected one or more phase transitions of water is located on the surface;
- the method further comprises estimating a thermal conductivity, a constituent material, and/or a temperature of the surface based on the at least one of the detected one or more phase transitions of water; and
- the surface comprises a roadway, a walkway, an automobile surface, an aircraft surface, a propeller surface, a combustion engine intake, and/or a crop surface.

* * * * *